(12) United States Patent
Chism, II

(10) Patent No.: US 8,300,227 B2
(45) Date of Patent: Oct. 30, 2012

(54) METHOD AND APPARATUS OF Z-SCAN PHOTOREFLECTANCE CHARACTERIZATION

(75) Inventor: William W. Chism, II, Austin, TX (US)

(73) Assignee: Xitronix Corporation, Austin, TX (US)

( * ) Notice: Subject to any disclaimer, the term of this patent is extended or adjusted under 35 U.S.C. 154(b) by 79 days.

(21) Appl. No.: 12/866,695

(22) PCT Filed: Feb. 13, 2009

(86) PCT No.: PCT/US2009/034045
§ 371 (c)(1),
(2), (4) Date: Aug. 6, 2010

(87) PCT Pub. No.: WO2009/102949
PCT Pub. Date: Aug. 20, 2009

(65) Prior Publication Data
US 2010/0315646 A1 Dec. 16, 2010

Related U.S. Application Data

(60) Provisional application No. 61/065,528, filed on Feb. 13, 2008.

(51) Int. Cl.
*G01N 21/55* (2006.01)
(52) U.S. Cl. ........................................................ 356/445
(58) Field of Classification Search .................. None
See application file for complete search history.

(56) References Cited

U.S. PATENT DOCUMENTS

| | | | |
|---|---|---|---|
| 4,634,290 A | 1/1987 | Rosencwaig et al. ............. 374/5 |
| 4,854,710 A | 8/1989 | Opsal et al. .................... 356/432 |
| 5,255,070 A | 10/1993 | Pollak et al. ................... 356/417 |
| 5,255,071 A * | 10/1993 | Pollak et al. ................... 356/417 |
| 5,260,772 A | 11/1993 | Pollak et al. ................... 356/417 |
| 5,270,797 A | 12/1993 | Pollak et al. ................... 356/417 |
| 7,391,507 B2 * | 6/2008 | Chism, II ......................... 356/32 |
| 2007/0097370 A1 | 5/2007 | Chism ............................ 356/432 |

OTHER PUBLICATIONS

Aspnes et al., "Resonant Nonlinear Optical Susceptibilty: Electrorflectance in the low0Field Limit," *Physical Review*, 5(10), 1972.
Aspnes, "Direct verification of the third-derivative nature of electroreflectance spectra," *Phys. Rev. Lett.*, 28:168-171, 1972.
Aspnes, "Modulation Spectroscopy," in *Handbook on Semiconductors*, 2,109, 1980.
Badakhshan et al., "Correlation between the photoreflectance response at $E_1$ and carrier concentration in $n$- and $p$-GaAs," *J. Appl. Phys.*, 69:2525, 1991.
Badakhshan et al., "Photoreflectance characterization of GaAs as a function of temperature carrier concentration, and near-surface electric field," *J. Vac. Sci. Tehnol. B*, 11(2):169-174, 1993.

(Continued)

*Primary Examiner* — Tu Nguyen

(57) ABSTRACT

A method of z-scan photo-reflectance characterization of semiconductor structures and apparatus for same has been developed. The method and apparatus provides the ability to independently measure electro-refractive and electro-absorptive nonlinearities that occur in conventional photo-reflectance signals. By performing a series of photo-reflectance measurements, each containing photo-modulated nonlinear optical signals, with the sample at a multiplicity of positions along the focal length of the probe light column, and with an aperture fixtured in the reflected probe path, precision characterization of both electro-refractive and electro-absorptive nonlinearities is attained. The Z-scan photo-reflectance method and apparatus characterizes spatial distortions of a coherent photo-reflectance probe light beam due to electro-refractive and electro-absorptive effects.

20 Claims, 14 Drawing Sheets

OTHER PUBLICATIONS

Baesso et al., "Thermal Lens Spectrometry to Study Complex Fluids," *Brazillian Journal of Physics*, 28(4), 1998.

Bindra et al., "Direct measurement of free carrier nonlinearity in semiconductor-doped glass with picosecond pump-probe Z-scan experiment," *Optics Communications*, 271(1):248-252, 2007.

Bindra et al., "Intensity dependence of Z-scan in semiconductor-doped glasses for separation of third and fifth order contributions in the below band gap region," *Optics Communications*, 168:219-225, 1999.

Borsch et al., "Diagnostics of optical nonlinearities: spatial beam distortion technique and its application to semiconductors and novel materials," *Proceeds of the SPIE—The International Society for Optical Engineering*, 52024(1): 128-136, 2003.

Ganeev et al., "Application of RZ-scan technique for investigation of nonlinear refraction of sapphire doped with Ag, Cu, and Au nanoparticles," *Optics Communications*, 253:205-213, 2005.

Ganeev et al., "Nonlinear optical characteristics of BSO and BGO photorefractive crystals in visible and infrared ranges," *Optical and Quantum Electronics*, 36:807-818, 2004.

Ganeev et al., "Reflection z-scan measurements of opaque semiconductor thin films," *Physica Status Solidi*, 202(1):120-125, 2005.

Ganeev et al., "Third-order nonlinearities of Bi12GeO20 crystal measured by nanosecond radiation," *Journal of Applied Physics*, 97:104303, 2005.

Ganeev, "Nonlinear refraction and nonlinear absorption of various media," *J. Opt. A: Pure Appl. Opt.*, 7:717-733, 2005.

Gomes et al., "Thermally managed eclipse Z-scan," *Optics Express*, 15(4), 2007.

Hunsche et al., "Influence of reflectivity on femtosecond trasmission spectroscopy," *Optics Communications*, 10:258-264, 1994.

Keldysh, "The Effect of a Strong Electric Field on the Optical Properties of Insulating Crystals," *Soviet Physics*, 34(7): 780-788, 1958.

Keldysh et al., "Polarization Effects in the Interband Absorption of Light in Semiconductors Subjected to a Strong Electric Field," *Sov. Phys.-Semicond.*, 3:876-884, 1970.

Kudrawiec et al., "Three beam photo-reflectance as a powerful method to investigate semiconductor heterostructures," *Thin Solid Films*, 450: 71-74, 2004.

Ma et al., "Two-color Z-scan technique with enhanced sensitivity," *Appl. Phys. Lett.*, 66(13):1581-1583, 1995.

Mansanares, "Optical Detection of Photothermal Phenomena . . . " in *Prog. Photototh. Sci. Tech . . .* , vol. 4, 2000.

Martinelli et al., "Measurement of refractive nonlinearities in GaAs above bandgap energy," *Appl. Opt.*, 39:6193-6196, 2000.

Martinelli, "Sensitivity-enhanced reflection Z-scan by oblique incidence of a polarized beam," Appl. Phys. Lett., 72:1427-4129, 1998.

Menard et al., "Single-beam differential z-scan technique," *Appl. Opt.*, 46:2119-2122, 2007.

Miller et al., "Band Gap-Resonant Nonlinear Refraction in III-V Semiconductors," *Phys. Rev. Lett.*, 47: 198, 1981.

Nahory et al., "Reflectance Modulation by the Surface Field in GaAs," *Phys. Rev. Lett.*, 21:1569-1571, 1968.

Opsal et al., "Thermal and plasma wave depth profiling in silicon," *Apply. Phys. Lett.*, 47: 498, 1985.

Opsal et al., "Temporal behavior of modulated optical reflectance in silicon," *J. Appl. Phys.*, 61(1):240-248, 1986.

Petris et al., "Strongly enhanced third order nonlinear response of periodically nano-structured silicon-on-insulator (SOI) measured by reflection Z-scan with fetosecond pulses," *Journal of Optoelectronics and Advanced Materials*, 8(4):1377-1380, 2006.

Petrov et al., "Reflection of a Gaussian beam from a saturable absorber," *Optics Communications*, 123:637-641, 1996.

Petrov, "Reflection Z-scan technique for the study of nonlinear refraction and absorption of a single interface and thin film," *J. Opt. Soc. Am.*, 13(7):1491, 1996.

Petrov et al., "Reflection Z-scan technique for measurements of optical properties of surfaces," *Appl. Phys. Lett.*, 66:1581-1583, 1995.

Philips et al., "Optical Constants of Silicon in the Region 1 to 10 ev," *Physical Review*, 120:37-38, 1960.

Philips et al., "Optical-Field on Thresholds, Saddle-Point Edges and Saddle-Point Exciton," *Phys. Rev. Lett*, 140:1716-1725, 1965.

Pollak, "Modulation Spectroscopy of Semiconductors" in *Handbook on Semiconductors*, 2:527-635, 1994.

Rosencwaig et al., "Comment on 'Spatially resolved defect mapping in semiconductors using laser-modualted thermo-reflecantance," *Appl. Phys. Lett.*, 1986.

Said et al. "Determination of bound-electronic and free-carrier nonlinearities in ZnSe, GaAs, CdTe, and ZnTe," *J. Opt. Sco. Am. B*, 9:405, 1992.

Seraphin et al., "Band-Structure Analysis from Electro-Reflectance Studies," *Phys. Rev.*, 145:628-636, 1966.

Seraphin et al., "Field Effect of the of the Reflectance in Silicon," *Phys. Rev. Lett.*, 15:107-110, 1965.

Seraphin et al., "Optical Field Effect in Silicon," *Phys. Rev. Lett.*, 15:104-107, 1965.

Shay, "Photoreflectance line shape at the fundamental edge in Ultrapure GaAs," *Physical Review B*, 2(4): 803-807, 1970.

Sheik-Bahae et al., "High-sensitivity, single beam n2 measurements," *Optics Letter*, 14: 955, 1989.

Sheik-Bahae et al., "Sensitive Measurement of Optical Nonlinearities Using a single beam," *IEEE Journal of Quantum Electronics*, 26:760, 1990.

Shen et al., "Dependence of the photoreflectance of semi-insulating GaAs on temperature and pump chopping frequency," *Appl. Phys. Lett.*, 52(24):2058, 1988.

Shen et al., "Dynamics of photoreflectance from undoped GaAs," *Appl. Phys. Lett.*, 59:321-323, 1991.

Shen et al., "Electric field distributions in a molecular-beam epitaxy $Ga_{0.83}Al_{0.17}As/GaAs$ structure using photoreflectance," *J. Vac. Sci Technol. B*, 7(4), 804, 1989.

Shen et al., "Generalized Franz-Keldysh theory of electromodulation," *Phys. Rev. B.*, 2:7097-7102, 1990.

Shen et al., "Photoreflectance study of surface Fermi level in GaAs and GaAIAs," *Appl. Phys. Lett.*, 57:2118-2120, 1990.

Stryland et al., "Z-Scan Measurements of Optical Nonlinearities," in Characterization Techniques and Tabulations for Organic Nonlinear Materials, M. G. Kuzyk and C. W. Dirk, eds., (Marcel-Dekker 1998), p. 655.

Vitkin et al., "Laser-induced photothermal reflectance investigation of silicon damaged by arsenic ion implantation," *Appl. Phys. Lett.*, 54:2392-2394, 1989.

Wang et al., "Optical Characteristics of semiconductor saturable absorber mirrors investigated by the reflection Z-scan technique," *Optics Communications*, 265:369-372, 2006.

Zhang et al., "Nonlinear Photoacoustic and Photothermal Phenomena in Semiconductors," in *Prog. Phototh. Sci. Tech . . .* , vol. 4, 2000.

Zhao et al., "Z-scan technique using top-hat beams," *Appl. Phys. Lett.*, 66:1581-1583, 1995.

\* cited by examiner

METHOD AND APPARATUS OF Z-SCAN PHOTOREFLECTANCE CHARACTERIZATION

CROSS-REFERENCE TO RELATED PATENT APPLICATIONS

This application is a national phase application under 35 U.S.C. §371 of International Application No. PCT/US2009/034045 filed 13 Feb. 2009, which claims priority to U.S. Provisional Patent Application Ser. No. 61/065,528 filed 13 Feb. 2008. The entire text of each of the above-referenced disclosures is specifically incorporated herein by reference.

BACKGROUND

1. Field of the Invention

The present invention relates to photo-reflectance characterization of semiconductor structures and, more particularly, to photo-reflectance beam spatial profiling techniques. The present invention provides methods and apparatuses to perform beam profiling of photo-reflectance light beams and to independently measure refractive and absorptive non-linearities occurring in photo-reflectance measurements.

2. Background of the Invention

High sensitivity measurement techniques are required for process control during the volume manufacture of electronic devices. One of the most useful techniques in this regard is an optical technique known as photo-reflectance, which may be used to rapidly, nondestructively and precisely characterize very small optical signatures related to the electronic properties of semiconductor nanostructures. Photo-reflectance techniques are routinely used to measure differential changes in reflectivity smaller than one part per million.

In conventional photo-reflectance, a pump laser beam is used to periodically modulate the carrier density in a semiconductor sample, and hence modulate one or more physical quantities (such as, for example, near surface electric fields), thereby inducing a periodic variation in the reflectivity of the sample, which is then recorded by use of a coincident probe light beam. In general, the photo-reflectance signal may be written:

$$\Delta R/R = \alpha \Delta \in_1 + \beta \Delta \in_2, \quad (1)$$

wherein $\Delta R/R$ is the normalized change in reflectivity, $\alpha \equiv 1/R \times (\partial R/\partial \in_1)$ and $\beta \equiv 1/R \times (\partial R/\partial \in_2)$ are the "Seraphin coefficients," which contain filmstack information, and $\Delta \in_1$ and $\Delta \in_2$ are the pump induced changes in the real and imaginary parts of the complex dielectric function, respectively. [B. O. Seraphin and N. Bottka, "Field Effect of the Reflectance in Silicon," *Phys. Rev. Lett.* 15, 104-107 (1965); J. C. Philips and B. O. Seraphin, "Optical-Field Effect on Thresholds, Saddle-Point Edges, and Saddle-Point Excitons," *Phys. Rev. Lett.* 15, 107-110 (1965); B. O. Seraphin, "Optical Field Effect in Silicon," Phys. Rev. 140, A 1716-1725 (1965); B. O. Seraphin and N. Bottka, "Band-Structure Analysis from Electro-Reflectance Studies," *Phys. Rev.* 145, 628-636 (1966); D. Aspnes, "Modulation Spectroscopy," in *Handbook on Semiconductors*, Vol. 2, edited by M. Balkanski, pp. 109 (North-Holland, Amsterdam, 1980) ("Aspnes 1980"); F. H. Pollak, "Modulation Spectroscopy of Semiconductors and Semiconductor Microstructures," in *Handbook on Semiconductors*, Vol. 2, edited by M. Balkanski, pp. 527-635 (North-Holland, Amsterdam, 1994). ("Pollak 1994")].

$\Delta \in_1$ and $\Delta \in_2$ contain all the optical information available concerning the response of the material to the external modulation of any physical parameter. For example, modulated changes in the electric field produce changes in the reflectance according to the relation:

$$\Delta R/R = 1/R \times (\partial R/\partial F) \Delta F, \quad (2)$$

wherein F is the electric field. Using Equations (1) and (2), $\Delta \in_1$ and $\Delta \in_2$ may be identified as:

$$\Delta \in_i = (\partial \in_i / \partial F) \Delta F, \quad (3)$$

which provides the relationship between the material optical response and the modulation of the external parameter, in this case the electric field.

The presence of an electric field is known to produce a redshift of semiconductor interband transitions. [L. V. Keldysh, "The Effect Of A Strong Electric Field On The Optical Properties Of Insulating Crystals," L. V. Keldysh, Soviet Physics—JETP 34(7), 788-780 (1958)]. This electric field effect produces a sharp third-derivative signature in the electro-reflectance and/or photo-reflectance spectrum at the position of the semiconductor interband transition. [Aspnes 1980; Pollak 1994]. The photoreflectance signal arises from the electro-modulation effect for probe wavelengths nearby to semiconductor interband transitions. [Aspnes 1980].

Effective application of photo-reflectance to provide process control of semiconductor electronic properties in volume manufacturing is dependent on certain constraints, including (i) the ability to modulate the near-surface electrical field in the region of interest, (ii) the sensitivity of the probe to changes in the electric field, and (iii) the practical realization of process control criteria, such as high measurement speed, repeatability, spot size, etc.

To appreciate these constraints, it is instructive to consider an industry accepted process control application of photo-reflectance. Historically, ion implant monitoring in volume silicon IC manufacturing was accomplished with a photo-reflectance technique using a 488 nm wavelength laser pump beam in conjunction with a 633 nm laser probe. In such a process, a pump laser beam of several milliwatts is focused to a micron spot on a silicon wafer, producing an induced charge density on the order of $10^{18}/cm^3$. The presence of carriers modifies the silicon dielectric function through the addition of a Drude carrier plasma term and through a small temperature rise (approximately 1° C.).

This "modulated optical reflectivity" signal arises from distinct physical effects—the external modulation of temperature and carrier plasma density—and therefore may be generally modeled by: $R/R = \Delta(\partial R/\partial T) \Delta T + (\partial R/\partial N) \Delta N$, wherein T is temperature, and N is carrier plasma density. [J. Opsal, and A. Rosencwaig, "Thermal and plasma wave depth profiling in silicon," *Appl. Phys. Lett.* 47, 498 (1985) ("Opsal 1985"); A. Rosencwaig, et al., "Comment on 'Spatially resolved defect mapping in semiconductors using laser-modulated thermoreflectance,'" *Appl. Phys. Lett.* 49, 301 (1986); Jon Opsal, et al., "Temporal behavior of modulated optical reflectance in silicon," *J. Appl. Phys.* 61, 240 (1987) ("Opsal 1987")]. Each term has a distinct dependence on wavelength, or dispersion. The plasma modulation contribution is generally modeled after the Drude effect and is proportional to the square of the probe wavelength. [Opsal 1985; Opsal 1987]. Thus, the Drude plasma dispersion effect is suppressed at shorter wavelengths and therefore measurement of Drude carrier modulation is preferred at longer wavelengths, such as, for example, in the near-IR. At 633 nm, only changes in the real part of the Si dielectric function are significant.

In such circumstance, the photo-reflectance signal then simplifies to: $\Delta R/R \cong \alpha \Delta \in_1$. In a typical scenario, the Seraphin coefficient is roughly $\alpha \approx 4 \times 10^{-2}$, and the change in the dielectric function due to the Drude carrier plasma is $\Delta\in_1 \approx -3\times10^{-3}$, producing a plasma contribution to the photo-reflectance signal of $\Delta R/R \cong -1\times10^{-4}$. As it turns out, near 600 nm, a thermal term of opposite sign nearly cancels the plasma contribution, resulting in observed signals on the order $1\times10^{-5}$ or less. [Opsal 1985]. Notwithstanding this circumstance, this historical implementation of photo-reflectance has provided a basic "go/no go" implant process monitoring capability in IC manufacturing. However, due to the 633 nm wavelength being far from any significant optical features in silicon, the probe has no sensitivity to internal electric fields and/or interband transition energies. [Opsal 1985]. This fundamental problem severely limits the usefulness of thermo-modulation and carrier modulation measurement methods.

Ideally, the photo-reflectance apparatus is configured in a manner such that a given physical property may be determined in a straightforward fashion. For example, a photo-reflectance technique developed by the Applicant teaches the implementation photo-reflectance in a manner effective to characterize strain and active dopant in semiconductor manufacturing. [U.S. Pat. No. 7,391,507, issued to William W. Chism II on Jun. 24, 2008, entitled "Method of photo-reflectance characterization of strain and active dopant in semiconductor structures" (incorporated herein by reference)].

In that photo-reflectance technique, photo-reflectance probe wavelengths nearby strong optical absorptions in the semiconductor band structure are utilized such that the photo-reflectance signal arises from modulation of the surface electric field (electromodulation). In particular, this technique attains sensitivity to the active electronic properties of Si nanostructures by using a probe wavelength near the "$E_1$" interband transition in Si, which occurs at a wavelength of approximately 375 nm. In the vicinity of such a transition, the induced changes in the dielectric function $\Delta\in_1$ and $\Delta\in_2$ may be written as the product of a free carrier energy and a third derivative of the semiconductor dielectric function: $\Delta\in=\partial^3(\omega^2\in)/\partial\omega^3\times U_F$, wherein $U_F$ is a free carrier energy, $\omega$ is the photon frequency (energy), and $\in$ is the complex dielectric functions $\in=\in_1+i\in_2$.

Thus, one reason for selecting the wavelength of the probe beam at 375 nm for Si lies in the sharp derivative form for $\Delta\in_1$ and $\Delta\in_2$. The electro-modulation component then becomes:

$$1/R\times(\partial R/\partial F)\Delta F=\text{Re}[(\alpha-i\beta)\times\partial^3(\omega^2\in)/\partial\omega^3)]\times U_F, \quad (4)$$

wherein $U_F=e_2h^2F^2/24\,m\omega^2$, e is the electronic charge, h is Planck's constant, F is the electric field, and m is the carrier effective mass. This sharp derivative form is large only nearby strong optical absorptions in the semiconductor band structure, and may be used to measure the location of interband transitions with great precision. This is what allows the photo-reflectance technique to precisely measure strain in nanoscale strained silicon layers, for example, since the Si $E_1$ transition energy undergoes a known shift under strain. Nearby to these strong optical absorptions, the amplitude of the photo-reflectance response also has excellent sensitivity to electric fields. The electric field of $U_F$ is the near surface electric field. This term is typically proportional to the surface carrier density, which may be understood from the (approximate) Poisson relation: $N=\in_o F^2/2\,eV$ wherein N is the carrier density, V is the built-in surface voltage, and $\in_o$ is the permittivity of the material.

In the wavelength range of approximately 360-380 nm, the electric field modulation effect dominates the photo-reflectance response of silicon. The thermo-modulation and/or carrier modulation contributions to the photo-reflectance signal are typically below the detection limit of the photo-reflectance apparatus. Moreover, because the photo-reflectance signal is highly sensitive to the near surface electrical fields, it may be used to precisely measure activated dopant in Si transistor structures.

Because the photo-reflectance signal takes the form of a sum of contributions from the change in refraction and absorption (see Equation (1), above), it was not possible to independently determine the changes in nonlinear refraction and nonlinear absorption, i.e., what portion of the photo-reflectance signal arises from $\Delta\in_1$ or $\Delta\in_2$. Accordingly, there is a need for a method and apparatus for independently determining the refractive and absorptive changes induced in photo-modulated reflectance as well as thermo-elastic effects.

"Z-scan" techniques based on the principles of spatial beam distortion are known to provide simple means to measure spatial beam distortion due to nonlinear refraction and absorption of materials. [M. Sheik-Bahae, et al., "High-sensitivity, single beam n2 measurements," *Optics Lett.* 14, 955 (1989); M. Sheik-Bahae, et al., "Sensitive Measurement of Optical Nonlinearities Using a Single Beam," *IEEE Journal of Quantum Electronics* 26, 760 (1990); A. A. Said, et al., "Determination of bound-electronic and free-carrier nonlinearities in ZnSe, GaAs, CdTe, and ZnTe," *J. Opt. Soc. Am. B* 9, 405 (1992); E. W. Van Stryland and M. Sheik-Bahae, "Z-Scan Measurements of Optical Nonlinearities," in Characterization Techniques and Tabulations for Organic Nonlinear Materials, M. G. Kuzyk and C. W. Dirk, Eds., pp. 655-692 (Marcel Dekker, 1998)].

Reflectance "z-scan" methods generally include performing sequence of reflected intensity measurements with a highly focused laser beam such that "self-lensing" occurs as the sample surface is passed through the focal region. The induced phase change (spatial distortion) of the reflected beam causes a differential intensity to be measured with an aperture fixtured in the far field of the probe beam. The "open aperture" reflection z-scan configuration is useful to measure nonlinear refraction in opaque semiconductors, whereas the "small aperture" reflection z-scan may be utilized to measure absorptive nonlinearities and/or thermo-elastic surface deformations. [D. V. Petrov, A. S. L. Gomes, and Cid B. de Araujo, "Reflection Z-scan technique for measurements of optical properties of surfaces," *Appl. Phys. Lett.* 65, 1067-1069 (1994); D. V. Petrov, "Reflection Z-scan technique for the study of nonlinear refraction and absorption of a single interface and thin film," *J. Opt. Soc. Am. B* 13, 1491-1498 (1996) ("Petrov 1996"); R. A. Ganeev and A. I. Ryasnyansky, "Reflection z-scan measurements of opaque semiconductor thin films," *Phys. Stat. Sol. A* 202, 120-125 (2005); R. A. Ganeev, "Nonlinear refraction and nonlinear absorption of various media," *J. Opt. A: Pure Appl. Opt.* 7, 717-733 (2005) ("Ganeev 2005")]. Z-scan techniques have been used in both transmission and reflectance configurations to measure nonlinear optical coefficients.

SUMMARY OF THE INVENTION

The present invention relates to a method and apparatus for independently determining the electro-modulation components of the photo-reflectance signal. The present invention provides a means to characterize photo-reflectance signals which arise from an interband resonant nonlinearity. The present invention provides a means for the independent determination of electro-refractive and electro-absorptive nonlinearities during such photo-reflectance measurements.

The method and apparatus of the present invention substantially departs from the conventional concepts and designs of the prior art, and in so doing, provides an apparatus primarily developed for rapid and precise characterization of nonlinear optical properties of semiconductor structures.

In general, in one aspect, the invention features a method of z-scan photo-reflectance characterization of a semiconductor structure. The method includes the step of (a) illuminating an area of a surface of the semiconductor structure using an amplitude modulated pump laser beam, wherein the pump laser beam includes at least one wavelength with energy greater than the smallest interband transition energy of a semiconductor material within the semiconductor structure, thereby inducing time periodic changes in electronic charge density within the semiconductor structure such that the electric field profile within the semiconductor structure obtains a time periodic modulation, and the semiconductor material within the semiconductor structure is subject to a time periodic modulation of interband transition energies. The method further includes the step of (b) illuminating a portion of the modulated electric field profile of step (a) with a separate probe laser beam, wherein the probe laser beam includes at least one wavelength nearby an interband transition energy of the semiconductor material within the semiconductor structure, and suitable for recording the induced changes in semiconductor material optical response which occur nearby to interband transition energies. The method further includes the step of (c) recording reflected alternating current probe light from the illumination of the semiconductor structure, wherein the alternating current probe light includes a photo-reflectance signal. The method further includes the step of (d) performing a series of photo-reflectance measurements of steps (a), (b), and (c), with the semiconductor structure at a multiplicity of positions along the focal length of the probe light column, wherein an aperture is fixtured in the far field of the probe laser beam. And, the method further includes the step of (e) using the information collected in steps (a), (b), (c), and (d) to determine a physical property of the semiconductor structure.

Implementations of the invention can include one or more of the following features:

The semiconductor structure can include at least one of the following materials: II-VI zincblende semiconductor material, silicon, silicon-germanium, III-V semiconductor material, gallium arsenide, gallium nitride, carbon, germanium, silicon carbide, boron, nitrogen, phosphorus, arsenic, and combination thereof.

The semiconductor structure can include at least one of the following semiconductor electronic interfaces: a p-n junction, a p+/p junction, a n-p junction, a n–/n junction, p-type ultra shallow junction, n-type ultra shallow junction, and combinations thereof.

The semiconductor structure can include at least on of the following fields: a surface band bending electric field, a near surface electric field arising from an electronic interface, and combinations thereof.

The method further can include determining changes in the photo-reflectance signal as a function of intensity or profile of the pump laser beam.

The wavelength of the pump laser can be one of the following: 830 nm, 780 nm, 633 nm, 532 nm, 473 nm, and 440 nm.

The method further can include determining changes in the photo-reflectance signal as a function of the intensity or profile of the probe laser beam.

The wavelength of the probe laser can be in the range (a) 360 nm to 380 nm or (b) 395 nm to 415 nm.

The aperture in the far field of the reflected probe beam can be fixtured to provide on-axis light transmission of about 20 percent.

The aperture in the far field of the reflected probe beam can be fixtured to provide on-axis light transmission of about 50 percent.

The aperture in the far field of the reflected probe beam can be fixtured to provide on-axis light transmission of about 100 percent.

The aperture in the far field of the reflected probe beam can be fixtured to provide on-axis light transmission in the range of 10 percent to 100 percent.

The method further can include (i) acquiring the photo-reflectance signal using an open aperture z-scan and (ii) determining pump induced nonlinear refraction from the photo-reflectance signal. This method can optionally also include that the surface carrier concentration is determined from the probe band flattening profile.

The shift of the probe beam phase front can be determined from a photo-reflectance probe signal acquired using a restricted aperture z-scan.

The method further can include (i) acquiring the photo-reflectance signal using an restricted aperture z-scan, and (ii) determining pump induced nonlinear absorption from the photo-reflectance signal.

Pump induced nonlinear absorption can be determined from the difference of open aperture and restricted aperture z-scan photo-reflectance curves.

The method further can include determining nonlinear refraction according to an empirically determined calibration curve.

The method further can include determining nonlinear absorption according to an empirically determined calibration curve.

The method further can include determining electronic charge density according to an empirically determined calibration curve.

The method further can include determining electric field according to an empirically determined calibration curve.

The method further can include monitoring electronic charge depth profile according to an empirically determined calibration curve.

The method further can include determining electric field depth profile according to an empirically determined calibration curve.

The method further can include determining a characteristic using z-scan photo-reflectance information. Such characteristic can be one of the following characteristics: position, amplitude, spectral width, and spectral shape of the semiconductor interband transition energy.

The method further can include using z-scan photo-reflectance information to determine pump induced electric field profile as a function of an offset. The offset can be one of the following: pump-probe focus offsets, transverse offsets, and combinations thereof.

In general, in another aspect, the invention features an apparatus for detecting physical properties of a semiconductor structure. The apparatus includes (a) a semiconductor structure with a reflecting surface. The apparatus further includes (b) a pump laser system. The pump laser system is operable (i) to provide an amplitude modulated laser beam with a modulation frequency in the range of 100 kHz to 50 MHz, (ii) to operate at optical powers of at least about approximately 5 mW, and (iii) to contain at least one wavelength with energy greater than the smallest interband transition energy of a semiconductor material within the semiconductor structure. The apparatus further includes (c) a probe laser system. The probe laser system is operable (i) to provide a continuous wave laser beam, (ii) to operate at optical powers of at most about approximately 15 mW, and (iii) to contain at least one wavelength nearby an interband transition energy of a semiconductor material within the semiconductor structure. The apparatus further includes (d) a photoreceiver. The photoreceiver is operable to generate an electrical current proportional to input intensity. The apparatus further includes (e) an optical system. The optical system is operable (i) to focus at least one of the amplitude modulated laser beam and the continuous wave laser beam onto a common focal position on a surface of the semiconductor structure of diameter at most 50 microns, (ii) to translate the common focal position through a distance of approximately 10 times the Rayleigh range of at least one of the amplitude modulated laser beam and the continuous wave laser beam, and (iii) to separate and direct probe light reflected from the semiconductor structure through an aperture fixtured in a far field of the continuous wave laser beam and into the photoreceiver. The apparatus further includes (f) a phase locked signal detection system. The phase locked signal detection system is operable to record output of the photoreceiver. The apparatus further includes (g) a computer that includes measurement and system control software.

Implementations of the invention can include one or more of the following features:

The optical system can include a telescoping lens arrangement. The telescoping lens can be operable to control pump-probe focal offset, and the telescoping lens arrangement can be fixtured in the input path of the amplitude modulated laser beam or the continuous wave laser beam.

The optical system can include a beam expander fixture in the reflected probe light path. The beam expander fixture can be operable to expand and collimate the probe beam before transmission through the aperture.

The probe laser wavelength can be approximately 375 nm.

The probe laser can be an external cavity tunable wavelength laser providing a multiplicity of wavelengths nearby to an interband transition energy of the semiconductor material within the semiconductor structure.

The apparatus further can include a dichroic beamsplitter. The dichroic beamsplitter can be operable to make the pump and probe laser beams collinear.

The apparatus further can include a 20× objective lens. The 20× objective lens can be operable to co-focus the collinear pump and probe laser beams onto an area of a surface of the semiconductor structure.

The apparatus further can include a 40× microscope objective lens. The 40× microscope objective lens can be operable to co-focus the collinear pump and probe laser beams onto an area of a surface of the semiconductor structure.

The computer can be operable to provide automated z-stepping and photo-reflectance data acquisition.

The computer can be operable to provide automated control setting of the aperture.

In general, in another aspect, the invention features a method of determining a physical property of a semiconductor structure. The method includes the step of (a) performing beam profiling of a photo-reflectance probe light beam using a plurality of photo-reflectance measurements. The method further includes the step of (b) utilizing the plurality of photo-reflectance measurements to measure non-linearities occurring in the optical response of the semiconductor structure. Such non-linearities are refractive non-linearities, absorptive non-linearities, and combinations thereof. The method further includes the step of (c) utilizing the measured non-linearities to determine the physical property of the semiconductor structure.

In view of the foregoing disadvantages inherent in the known types of optical spectroscopy now present in the prior art, the present invention provides a method and apparatus wherein the same can be utilized for the characterization of nonlinear optical properties of semiconductor structures including independent determination of electro-refractive and electro-absorptive non-linearities.

Implementations of the invention can include one or more of the following features:

The step of measuring the non-linearities can include (i) measuring refractive non-linearities occurring in the plurality of the photo-reflectance measurements, and (ii) independently measuring absorptive non-linearities in the plurality of the photo-reflectance measurements.

The beam profiling can be pump induced electro-modulation profiling, probe band flattening profiling, and combinations thereof.

The step of performing the beam profiling can include utilizing an open aperture, utilizing a restricted aperture, or utilizing both.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1:
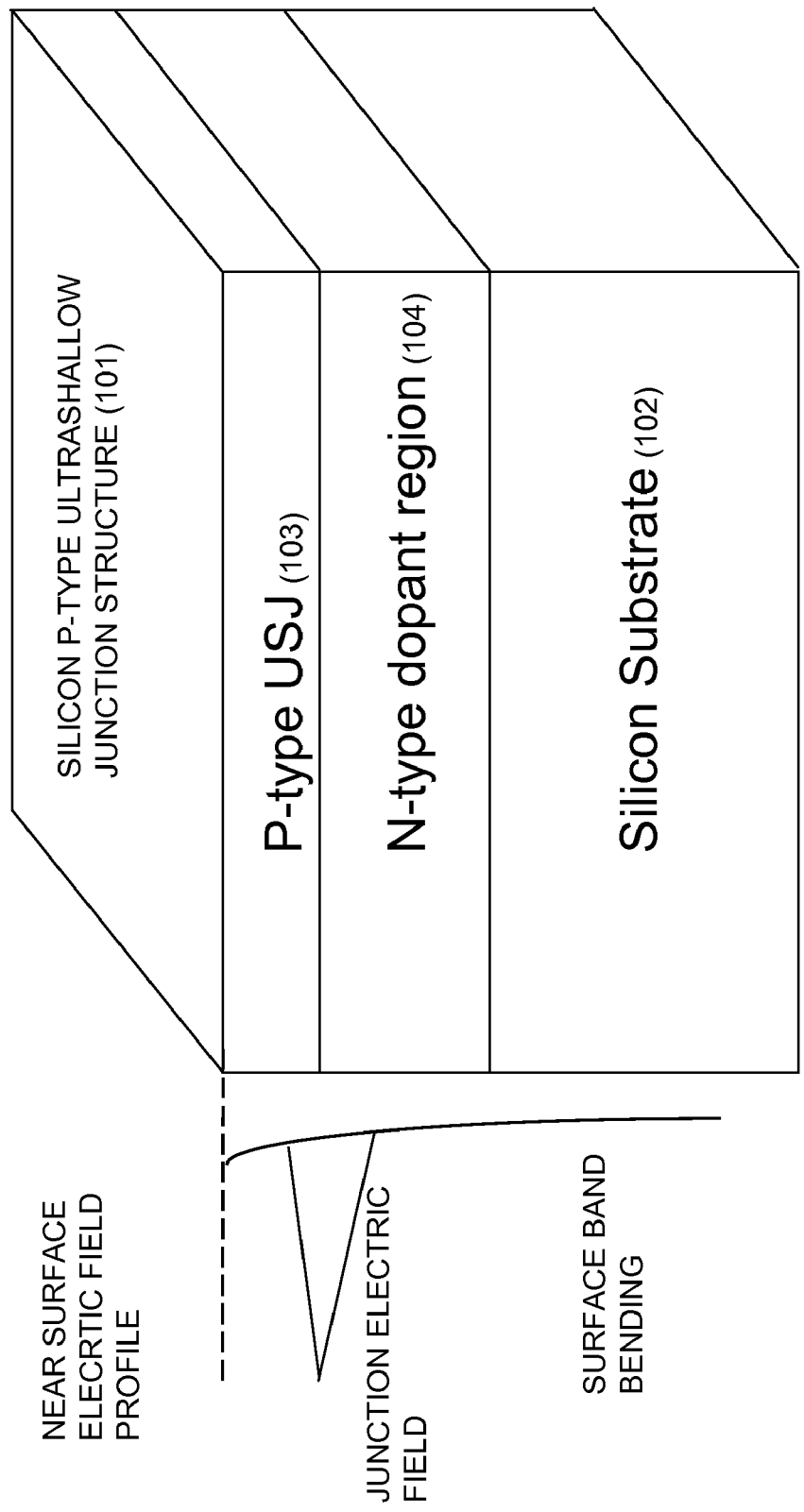
FIG. 1 contains, in an exaggerated view, an exemplary "p-type" Ultra-Shallow Junction (USJ) silicon filmstructure that may be characterized using the photo-reflectance technique of the present invention. The p-type USJ silicon filmstructure comprises a crystalline silicon substrate that is implanted with 40 KeV arsenic (As) at a dose of approximately $4 \times 10^{13}/cm^2$, followed with a 500 eV boron (B) implant, and annealed using a milli-second flash annealing technique. This forms a p-n junction between the p-type USJ structure and the n-type implant. At this junction a strong near surface electric field forms, as shown schematically in FIG. 1.

The following discusses use of the method of z-scan photo-reflectance characterization of semiconductor structures and an apparatus for same for characterization of electro-refraction and electro-absorption of silicon semiconductor structures. It is understood that the method of the present description may be used to analyze any semiconductor structure, the discussion of exemplary silicon structures considered to be exemplary only and in no way limiting in scope. It should be appreciated that the present invention provides many applicable inventive concepts that may be embodied in a variety of specific contexts. The specific embodiments discussed herein are merely illustrative of specific ways to make and/or use the invention and are not intended to delimit the scope of the invention.

The present invention utilizes the characteristic that the electro-modulation signal described above arises from an interband resonant nonlinearity. The pump induced change in refractive index $\Delta n$ may be written $\Delta n = n_2/2 \times I_{pump}$, and the pump induced change in extinction coefficient $\Delta k = k_2/2 \times I_{pump}$. Here, $I_{pump}$ contains the excitation profile and may be written $I_{pump} = F^2 \times |f(\rho,z)|^2$, wherein f is the pump induced electromodulation profile as a function of transverse distance $\rho$ and depth z. The relation with the (third-order) nonlinear susceptibility $\chi^{(3)} = \chi^{(3)}_R + i\chi^{(3)}_I$ is given by $\chi^{(3)}_R = n_o^2 \epsilon_o c n_2$ and $\chi^{(3)}_I = n_o^2 \epsilon_o c k_2$, wherein $n_o$ is the linear index of refraction, c is the speed of light, $n_2$ is the effective nonlinear index of refraction, and $k_2$ is the effective nonlinear extinction coefficient.

Given the different wavelengths of the pump and probe beam, the spatial beam measurement techniques disclosed herein have certain features in common with the "two-color" z-scan technique. [H. Ma and Cid B. de Araujo, "Two-color Z-scan technique with enhanced sensitivity," *Appl. Phys. Lett.* 66, 1581-1583 (1995) ("Ma 1995")]. However, the nonlinearity is not due to third-order resonance with the pump photon energy, but rather arises from the effective DC (MHz) electric field modulation, i.e., it is an interband resonant third order nonlinearity [(D. A. B. Miller, et al., "Band Gap-Resonant Nonlinear Refraction in III-V Semiconductors," *Phys. Rev. Lett.* 47, 198 (1981)]. The modulated photo-reflectance signal itself may be identified with the (nonlinear) electro-refraction and electro-absorption. Thus, the present invention provides a means for the independent determination of electro-refractive and electro-absorptive nonlinearities during such photo-reflectance measurements.

The method and apparatus include performing photo-reflectance measurements with the photo-reflectance apparatus configured such that the position of the sample surface is scanned through the focus of the probe light beam and/or pump laser beam waists. Spatial distortion of the probe beam is analyzed in the far field through the use of an adjustable aperture. This method and apparatus provides for enhanced sensitivity to the electro-modulation components of the photo-reflectance signal.

The general purpose of the present invention, which will be described subsequently in greater detail, is to provide a method and apparatus that can independently measure photo-reflectance signals arising from electro-refractive and electro-absorptive effects.

An underlying principle of the method and apparatus is to analyze spatial distortions induced by electro-refractive and electro-absorptive contributions to the photo-reflectance (PR) signal. By performing a sequence of photo-reflectance measurements with the pump focal position offset along direction of light propagation "z," a z profile or "z-scan" of pump induced electro-refractive and electro-absorptive components of the PR signal is attained.

In an embodiment of the present invention, the measured photo-reflectance signal, in addition to being dependent on the probe beam geometry, depends on pump beam parameters, such as the pump beam waist size, transverse offset, and possible focal separation (longitudinal offset). These parameters are included in the expression for the far field probe beam profile. These z-scan photo-reflectance measurements may be accomplished with Gaussian profile beams or with other beam profiles such as the "top-hat" radial intensity distribution. [W. Zhao and P. Palffy-Muhoray, "Z-scan technique using top-hat beams," *Appl. Phys. Lett.* 63, 1613 (1993); M. Martinelli, L. Gomes, and R. J. Horowicz, "Measurement of refractive non-linearities in GaAs above bandgap energy," *Appl. Opt.* 39, 6193-6196 (2000)]. Sensitivity may be enhanced by using oblique angles of incidence and/or selected polarizations [M. Martinelli, "Sensitivity-enhanced reflection Z-scan by oblique incidence of a polarized beam," *Appl. Phys. Lett.* 72, 1427-1429 (1998); L. V. Keldysh, O. V. Konstantinov, and V. I. Perel, "Polarization Effects in the Interband Absorption of Light in Semiconductors Subjected to a Strong Electric Field," *Soviet Physics-Semiconductors* 3, 876-884 (1970)].

In one embodiment, the present invention generally comprises a diode laser pump beam of approximately 15 mW operating in the NIR-VIS. The pump beam is amplitude modulated by a signal generator operating in the range of 100 kHz-50 MHz. The probe beam comprises a diode laser beam of approximately 5 mW, with wavelength selected to coincide with a suitable interband transition energy of the semiconductor sample. The pump and probe may be made collinear by use of a dichroic beamsplitter. The pump and probe are directed to nearby micrometer scale spots on the sample. The pump and probe focal positions may be independently controlled such that the apparatus provides a means to step the focus through a distance approximately ten (10) times the Rayleigh range of either beam without clipping. The reflected probe light is color separated and projected through a beam expander, through an adjustable aperture, and focused onto a high speed photo-diode. The sample position is scanned through sequence of z positions, the total range of the scan being approximately ten times the Rayleigh range of probe beam at focus. At each sample position, the reflected probe light PR signal is recorded using phase-locked detection and is stored as function of sample position, pump-probe offset, pump intensity, angle of incidence, probe wavelength and/or probe polarization. An open aperture z-scan may be performed and analyzed to measure the electro-refractive effect. The open-aperture z-scan data may be used to determine the nonlinear index of refraction and/or physical parameters. A small aperture z-scan may be performed and analyzed to measure the electro-absorptive effect. Thus, independent determination of electro-refractive and electro-absorptive components of the PR signal is attained.

As discussed, an amplitude modulated light beam incident on the surface on a semiconductor structure causes changes in its optical properties. The photo-reflectance signal can be recast as follows:

$$\Delta R/R = \alpha' \Delta n + \beta' \Delta k, \quad (5)$$

wherein $\Delta n$ is the pump induced change in the index of refraction, $\Delta k$ is the pump induced change in the extinction coefficient, and the Seraphin coefficients are now defined as $\alpha' \equiv 1/R(\partial R/\partial n) = \alpha \times 2n$, and $\beta' \equiv 1/R(\partial R/\partial k) = \beta \times 2n$ (which follows from the relation $\in = (n+ik)^2$).

From this, the photo-reflectance signal contains the contribution of the nonlinear refraction and absorption. In particular, $\Delta n \equiv n_2/2 \times I_{pump}$ and $\Delta k \equiv k_2/2 \times I_{pump}$ are defining relations for $n_2$ and $k_2$, the effective nonlinear refraction and extinction, respectively. The nonlinear dependence on surface electric field may be seen explicitly in the (carrier) free energy term $U_F = e^2 h^2 F^2/24\, m\omega^2$.

Because the PR signal of Equation (1) is a sum of these contributions, conventional PR measurements cannot distinguish between the nonlinear refraction and the nonlinear absorption. This is one reason why a method and apparatus to independently determine these nonlinear contributions is desirable.

Modifications of the spatial intensity distribution of a laser beam reflected from a nonlinear material can be used to establish independent characterization of the nonlinear refraction and absorption in photo-reflectance measurements. By way of example, consider the reflection of light from the surface of a nonlinear optical material. Assuming the situation is reflection from a single planar interface (such as a bulk silicon substrate), and neglecting thermal expansion, the complex Fresnel reflection coefficient takes the form:

$$r(z,\rho) = \{[(n+\Delta n) + i(k+\Delta k) - 1]/[(n+\Delta n) + i(k+\Delta k) + 1]\}, \quad (6)$$

wherein z refers to the longitudinal radial intensity distribution of the pump beam, and $\rho$ refers to the transverse radial intensity distribution of the pump beam.

This Equation (6) illustrates that a phase change of the reflected wave is caused by the nonlinear absorption, whereas the nonlinear refraction causes an amplitude change. [Petrov 1996]. In particular:

$$r \approx r_o + r_1[\Delta n + ik],$$

wherein:

$$r_o = [n+ik-1]/[n+ik+1], \text{ and}$$

$$r_1 = 2/(n+1+ik)^2.$$

The "$r_o$" term contains the linear reflectivity, while the "$r_1$" term contains the photo-reflectance signal.

Now, by way of example, consider an incident Gaussian intensity distribution propagating along the z axis, wherein z=0 is taken as the beam waist. Taking into account the pump induced reflection change, the reflected probe light electric field distribution at the sample surface is:

$$E_r(z,\rho) = E_i \times \overline{\omega}_o / \overline{\omega}(z) \times \exp[-i\phi(z) - i\pi/\lambda R(z)] \times \exp(i2\pi z/\lambda)\{r_o \exp[-\rho^2/\overline{\omega}^2(z)] + r_1(\Delta n + i\Delta k)/[1+(z/z_o)^2] \times \exp[-3\rho^2/\overline{\omega}^2(z)]\}, \quad (7)$$

wherein:

$E_i$ is the incident probe light field inside the sample, $\lambda$ is the probe wavelength, $\overline{\omega}_o$ is the beam waist radius, $z_o = \pi \overline{\omega}_o^2/\lambda$ is the Raleigh diffraction range, $\overline{\omega}(z) = \overline{\omega}_o[1+(z/z_o)^2]^{1/2}$ is the beam radius, $R(z) = z[1+(z_o/z)^2]$ is the wavefront radius of curvature, and $\phi(z) = \arctan(z/z_o)$.

This is the expression for the electric field distribution of a reflected Gaussian probe beam in terms of its beam parameters and the pump induced electro-refraction and electro-absorption profile. This field distribution results in an on-axis far field intensity distribution at an aperture plane located a distance d from the beam waist, written as a function of sample position z, of the form:

$$I_r(z)=I_i \times |r_o/G_o(z)+r_1/G_1 \times (\Delta n+i\Delta k)/[1+(z/z_o)^2]|^2, \quad (8)$$

wherein $G_o(z)$ and $G_1(z)$ are terms that depend only on (probe) beam parameters d, z, $z_o$, and $\bar{\omega}_o$. [Petrov 1996]. This term is just $I_{DC}+\Delta I_{AC}$ contained in the output probe beam of conventional photo-reflectance technique. Dividing by $I_i \times |r_o/G_o(z)|^2$, and equating $\Delta I/I$ with $\Delta R/R$, the on-axis intensity distribution includes a term proportional to $\Delta k$ (in addition to $\Delta n$), which implies the electro-absorption is responsible for an on axis phase change.

When the aperture is open such that all the photo-reflectance probe light is incident on the detection photo-diode, the photo-reflectance signal takes the form:

$$\Delta R/R = \text{Re}\{r_1/r_o\} \times \Delta n/[1+(z/z_o)^2]. \quad (9)$$

[Petrov 1996]. This indicates the surface contribution to open-aperture Z-scan photo-reflectance signal is affected only by the nonlinear refraction. The effect of interference with additional reflections originating from additional filmstack interfaces or the bulk alters this conclusion by reason of the fact that interference may mix $\Delta k$ contributions into the open aperture z-scan. [Petrov 1996]. Numerical evaluation of the above equations demonstrates that when the apparatus is capable of measuring photo-reflectance signals of the order $10^{-6}$, optical nonlinearities of $\Delta n \approx \Delta k \approx 1 \times 10^{-7}$ are observable.

Thus, for pump intensities $I_{pump} \approx 1 \times 10^5$ W/cm$^2$, effective nonlinear indices of refraction $n_2$ and/or nonlinear extinction coefficients $k_2$ greater than $\approx 2 \times 10^{-12}$ cm$^2$/W can be measured. For the symmetric open aperture z-scan curves, Equation (9) may be used to estimate $n_2 \approx \Delta R/R_{max} \times (n^2-k^2-1)/I_{pump}$. For the on-axis small aperture z-scan curves, Equation (8) may be used to determine the relationship of the amplitude of the "peak-valley" z-scan signature $\Delta T_{p-v}$ with the on-axis phase change $\Delta \phi$. Also, the open aperture curve may be subtracted from the restricted aperture cure to amplify $\Delta T_{p-v}$.

Accordingly, it is possible to measure the nonlinear refraction independently from the nonlinear absorption in photo-reflectance by performing an open-aperture z-scan photo-reflectance measurement including a series of photo-reflectance measurements with the sample at a multiplicity of positions along the focal length of the probe light column. The sample position is scanned through sequence of z positions, the total range of the scan being approximately ten (10) times the Rayleigh range of probe beam at focus. At each sample position, the reflected probe light PR signal undergoes a signal processing procedure and is stored as function of sample position, aperture size, pump intensity, angle of incidence, and probe laser parameters. The phase of the PR measurement (i.e., whether the reflectivity of the sample increases with pump intensity, or decreases) determines the sign of the nonlinear refraction.

Once this measurement is complete, a second small-aperture z-scan measurement (which contains both refractive and absorptive nonlinearities) can be effected by performing a series of photo-reflectance measurements with the sample at a multiplicity of positions along the focal length of the probe light column with an aperture fixtured in the reflected probe light path. The value of the nonlinear index of refraction from the open-aperture z-scan is input to the analysis of the on-axis intensity distribution to extract an independent measurement of the nonlinear absorption.

The difference of the open aperture and small aperture curves provides the relative spatial beam distortion of the on-axis z-scan photo-reflectance signal. The electro-absorptive component of the PR signal can be determined from the amplitude of the small aperture "peak-valley" signature $\Delta T_{p-v}$ and the aperture size. [See Petrov 1996]. The same (or a similar) approach can also be applied to the precision characterization of thermo-elastic effects as well, as thermal expansion of the semiconductor surface generates an on-axis phase change analogous to the nonlinear absorption [See Petrov 1996].

By this, the probe photo-reflectance probe beam parameters, including the pump induced electro-modulation profile, are analyzed. Further, the z-scan photo-reflectance technique taught herein may be accomplished with Gaussian profile beams or with other beam profiles such as the "top-hat" radial intensity distribution, as shown in the prior art. Further, sensitivity may be enhanced by using oblique angles of incidence and/or selected polarizations, as shown in the prior art.

FIG. 1 contains, in an exaggerated view, an exemplary "p-type" Ultra-Shallow Junction (USJ) silicon filmstructure 101 that may be characterized using the photo-reflectance technique of the present invention. The p-type USJ silicon filmstructure 101 comprises a crystalline silicon substrate 102 that is implanted with 40 KeV arsenic (As) at a dose of approximately $4 \times 10^{13}$/cm$^2$, followed with a 500 eV boron (B) implant, and annealed using a milli-second flash annealing technique. This forms a p-n junction between the p-type USJ structure 103 and the n-type implant 104. At this junction a strong internal electric field forms, as shown schematically in FIG. 1. Exemplary embodiments of silicon semiconductor structures include various junctions such as p$^+$/p and n$^-$/n junctions and various silicon (Si) and silicon germanium (SiGe) substrates.

Figure 2:
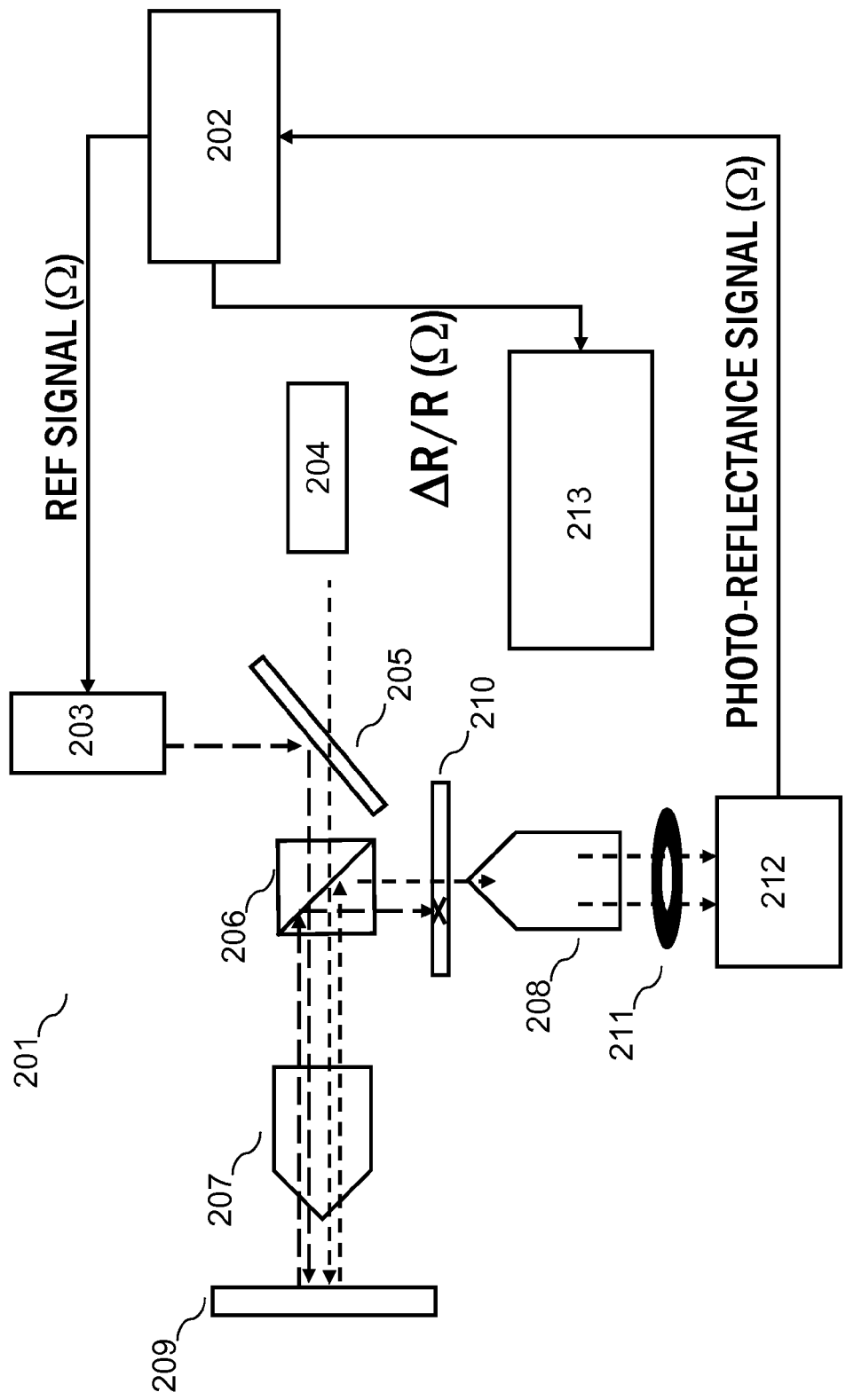
FIG. 2 shows z-scan photo-reflectance arrangement that may be used to perform z-scan photo-reflectance measurements in accordance with the present invention

In accordance with an embodiment of the present invention as illustrated in FIG. 2, z-scan photo-reflectance may be used to measure the reflected spectra from a silicon substrate, or any other semiconductor structure, in order to characterize the photo-modulated nonlinear optical properties of the semiconductor structure. As shown in FIG. 2, z-scan photo-reflectance arrangement 201 comprises: (a) a lock-in amplifier 202, which drives a pump diode laser 203, (b) a probe diode laser 204, a dichroic beamsplitter 205, an optical system, which may comprise a polarization beamsplitter 206, a microscope objective 207, and/or a beam expander 208, a reflecting semiconductor sample 209 (with adjustable z position), a color filter 210, an adjustable aperture 211, a photodiode 212, and a computer (or other controller) 212 suitable to control measurement parameters and record reflectivity changes.

In an exemplary embodiment of the present invention, the pump laser 203 intensity is directly modulated using a 1 volt peak to peak square wave reference signal from the lock-in amplifier 202. The pump and probe beams (from the pump laser 203 and probe laser 204, respectively) are made collinear through the use of the dichroic beamsplitter 205. The collinear beams are then focused onto the reflecting sample 209 using the optical system (including, for example, a microscope objective lens 207 or an achromatic focusing lens and collected using a collection lens). The pump light is color filtered using the color filter 210. The probe photo-reflectance beam, containing the modulated reflectivity of the sample, is projected through a beam expander 208 and then through an adjustable aperture 211, focused into the high-speed photo-diode 212 and converted to electrical current. This current is passed to the lock-in amplifier 202, which measures the amplitude and phase of the reflectivity change. This information is transmitted to the computer/controller 213, which records the components of the differential change in reflectivity vector (AC, DC, Phase) as a function of beam longitudinal position. This comprises an open-aperture z-scan. The computer/controller 213 then records the differential change in reflectivity as a function of the z position of the sample with the small aperture condition (approximately 10-50% throughput at focus), thereby providing the "on-axis" z-scan photo-reflectance information. The "open aperture" and the "on-axis" z-scan curves may be differenced to amplify electro-absorptive effects.

The pump laser diode can be a continuous wave laser diode with photon energy at or above the band gap of the semiconductor under investigation. For instance, for silicon, the band gap occurs at approximately 1100 nm wavelength. Pump wavelengths in the range 440 nm to approximately 1100 nanometers are suitable for silicon semiconductor material, with the shorter wavelengths preferable when characterizing silicon-on-insulator type substrates. Pump wavelengths of 830 nm, 780 nm, 633 nm, 532 nm, 473 nm, and 440 nm are convenient.

In an embodiment of the present invention, the pump wavelength is approximately 830 nm, and the pump laser power is approximately 16 mW. In this embodiment, the pump power ranges from approximately 10 mW to approximately 50 mW, with greater powers preferable when characterizing silicon-on-insulator type substrates. The DC pump laser intensity may be controlled by a controller (which may be computer/controller 213 or some other computer/controller). The pump amplitude may be modulated with an external function generator and with a reference signal supplied to the lock-in amplifier 202, or with an internal modulation signal generated by the lock-in amplifier 202. In this embodiment, the pump laser 203 is directly modulated at high frequency by the internal reference signal from the lock-in amplifier 202. The driving frequency varies from approximately 100 kHz to 50 MHz.

The pump laser diode in embodiments of the present invention include diode lasers emitting in the NIR-VIS wavelength range operating at powers of approximately 5 mW or above. It is also possible to configure embodiments of the present invention with pump wavelength of 325 nm, however, the pump beam must be externally modulated and steps must be taken to remove any photo-luminescence signal.

The pump laser beam may be modulated externally through use of an electro-optic or acousto-optic amplitude modulation arrangement. The probe light source comprises a continuous wave laser diode with photon energy at or near an interband transition energy of the semiconductor under investigation. For silicon, the longest wavelength at which such a suitable interband transition occurs is approximately 375 nm.

The method and apparatus of the present invention is generally applicable to photo-reflectance probe laser beams of wavelength nearby a semiconductor interband transition, such that the photo-reflectance arises from the electro-modulation effect. In an embodiment of the present invention, the probe wavelength is approximately 360-380 nm and the semiconductor material is silicon or a silicon-germanium alloy. The probe laser power is approximately 5-12 mW. Probe laser diodes include diode lasers emitting in the VIS-UV wavelength range operating at powers of approximately 15 mW or less. Probes in these embodiments can include tunable diode lasers, such as external cavity diode lasers or temperature tunable diode lasers.

In embodiments of the present invention, the pump and probe beams are made collinear through the use a dichroic beamsplitter. The collinear beams are focused onto the sample using a focusing arrangement, and the specularly reflected probe beam is collected and passed through the aperture and focused onto the detection photo-diode. Once the probe beam is reflected from the sample surface, it has an AC amplitude modulation containing the photo-modulated modulated nonlinear optical properties of the sample. Thus, the photodiode output contains electrical currents proportional to the probe signal.

The DC signal from the photodiode is proportional to $I_o R$, while the AC signal is proportional to $I_o \Delta R$. In order to measure $\Delta R/R$, the intensity $I_o$ must be normalized. This is accomplished by dividing the AC signal by the DC signal. Typical amplitudes of $\Delta R/R$ for the exemplary embodiment are on the order $\sim 10^{-2}$-$10^{-5}$. Phase sensitive measurement is performed on the photodiode output and the computer/controller 213 records the measurement photocurrents. The computer/controller 213 controls the sample z position, aperture position, pump laser intensity, and probe laser parameters (such as wavelength, polarization, and/or power). $\Delta R/R$ is recorded as a function of z position, aperture, pump intensity, and probe laser parameters. Thus, embodiments of the present invention (such as shown in FIG. 2) are suitable for z-scan photo-reflectance characterization of semiconductor structures. These embodiments include alterations to the arrangement that do not alter the fundamental z-scan photo-reflectance characterization signal.

Figure 3:
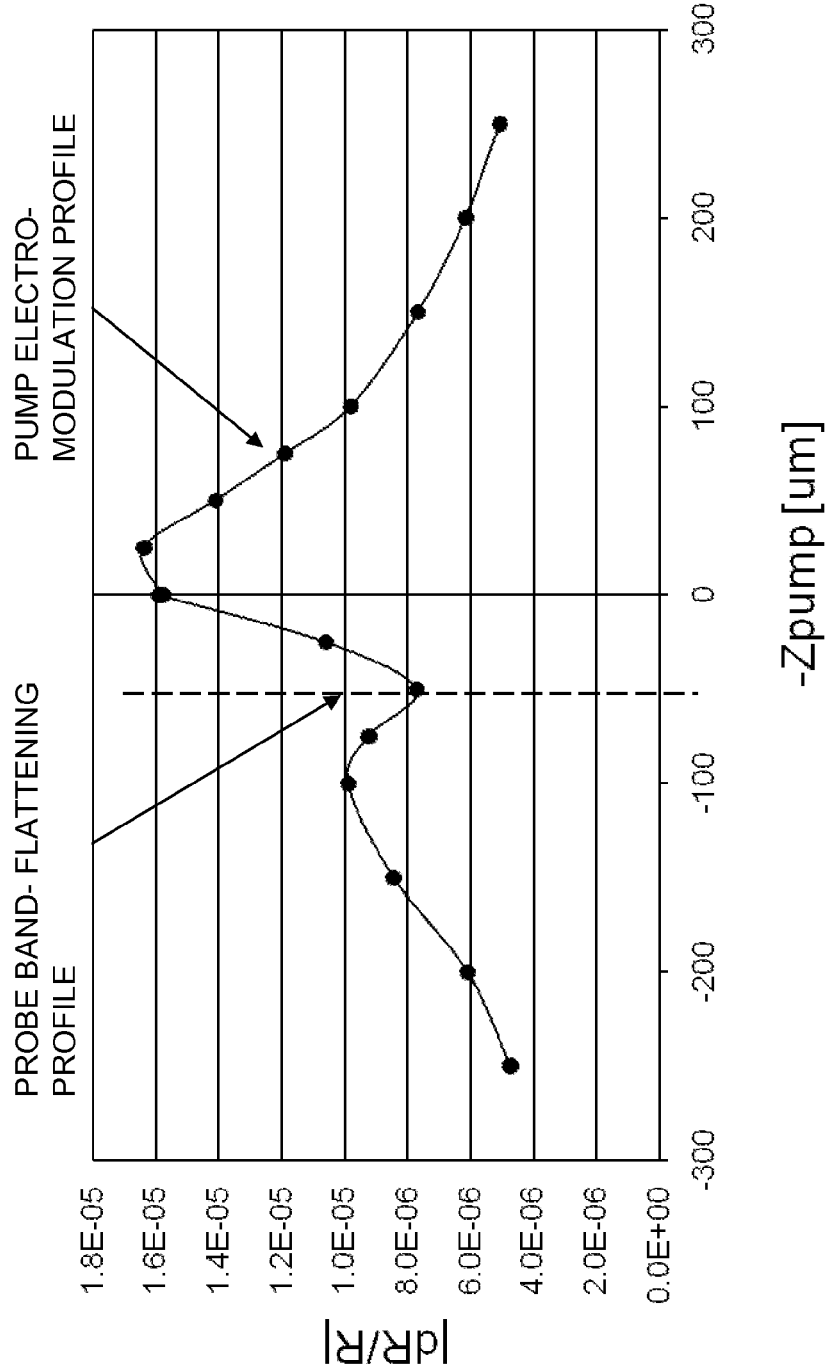
FIG. 3 is a curve generated from data taken in accordance with an embodiment of the present invention, wherein: (i) the waist of the probe beam is fixed offset positive 40 microns from the waist of the pump beam; and (ii) photo-reflectance measurements are made at a multiplicity of pump waist positions with respect to the sample surface.

FIG. 3 is a curve generated from data taken in accordance with an embodiment of the present invention, wherein: (i) the waist of the probe beam is fixed offset positive 40 microns from the waist of the pump beam; and (ii) photo-reflectance measurements are made at a multiplicity of pump waist positions with respect to the sample surface.

Figure 4:
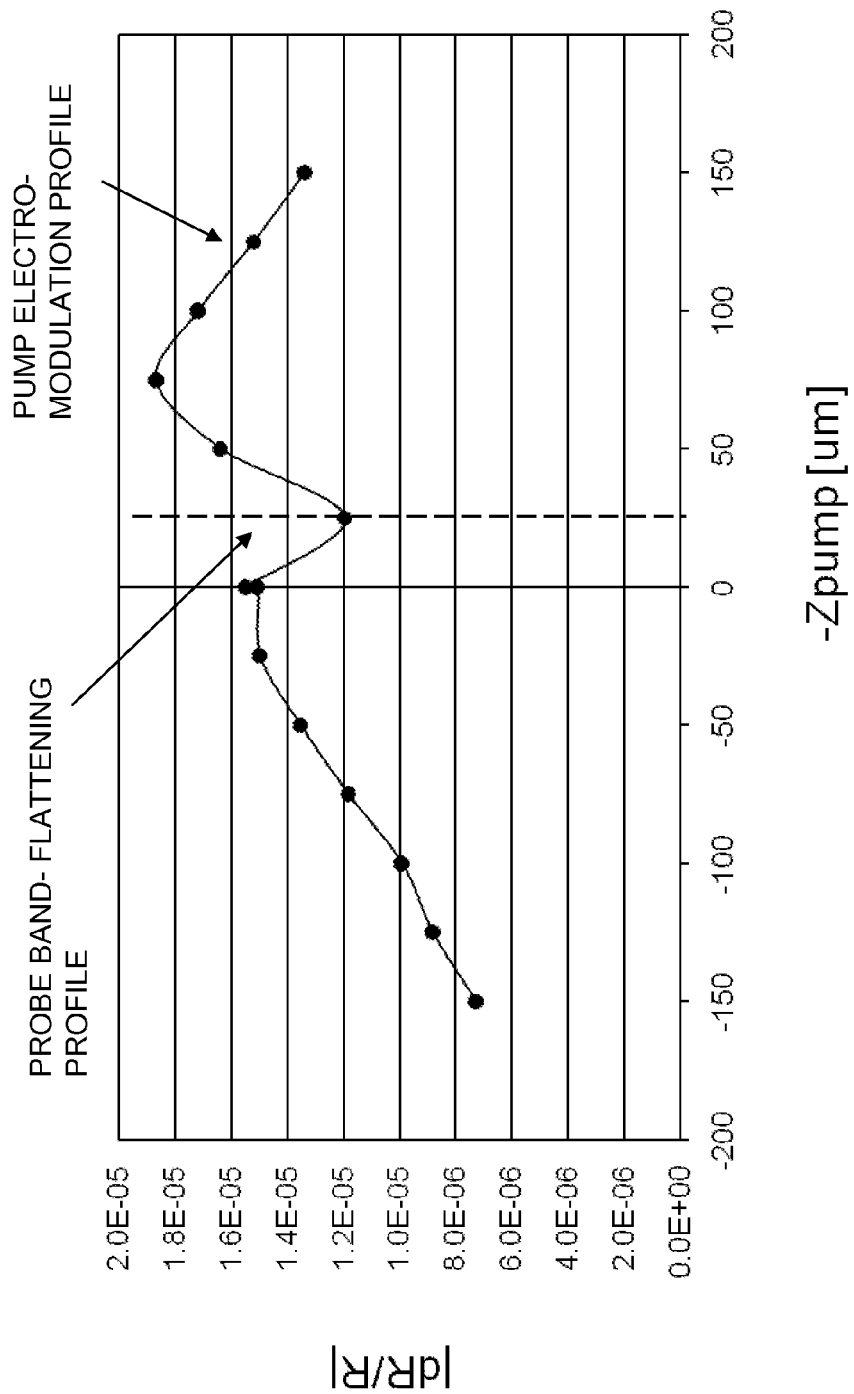
FIG. 4 is a curve generated from data taken in accordance with an embodiment of the present invention wherein: (i) the waist of the probe beam is fixed equal to the waist of the pump beam; and (ii) photo-reflectance measurements are made at a multiplicity of pump waist positions with respect to the sample surface.

FIG. 4 is a curve generated from data taken in accordance with an embodiment of the present invention wherein: (i) the waist of the probe beam is fixed equal to the waist of the pump beam; and (ii) photo-reflectance measurements are made at a multiplicity of pump waist positions with respect to the sample surface.

Figure 5:
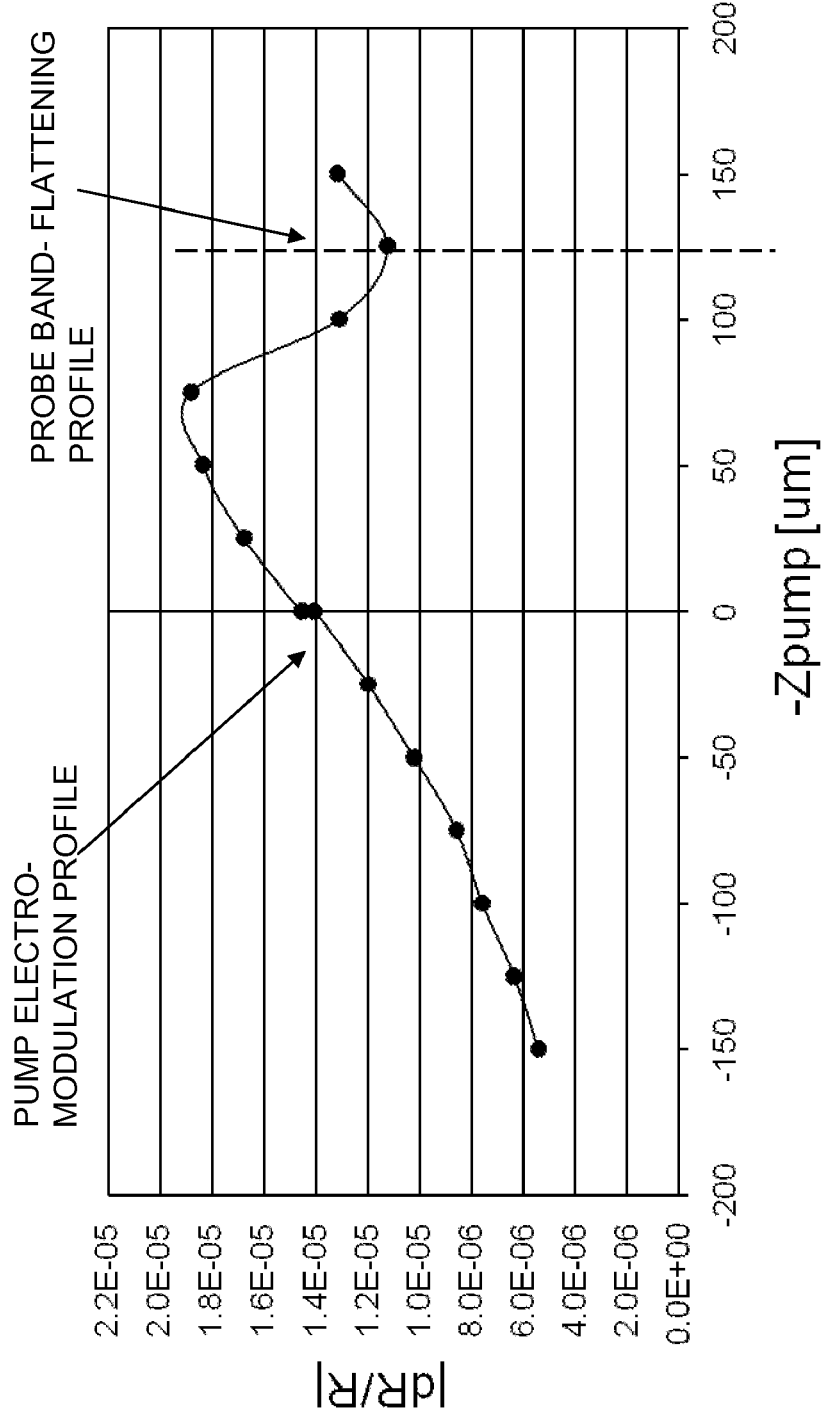
FIG. 5 is a curve generated from data taken in accordance with an embodiment of the present invention wherein: (i) the waist of the probe beam is fixed offset negative 40 microns from the waist of the pump beam; and (ii) photo-reflectance measurements are made at a multiplicity of pump waist positions with respect to the sample surface.

FIG. 5 is a curve generated from data taken in accordance with an embodiment of the present invention wherein: (i) the waist of the probe beam is fixed offset negative 40 microns from the waist of the pump beam; and (ii) photo-reflectance measurements are made at a multiplicity of pump waist positions with respect to the sample surface.

Each of the curves of FIGS. 3-5 was performed utilizing a photo-reflectance pump and probe beam focused and recollected through a 20× achromatic microscope objective. The focal positions of the pump and probe were controlled with independent telescoping lens arrangements in either input beam path. This allowed fine control of the respective beam collimations and directions, thereby providing precision control pump-probe transverse and focal offsets. The Z-scan photo-reflectance curves were performed without clipping the probe beam, i.e., each curve is an "open-aperture" curve. They reveal a smooth "dip" in the photo-reflectance curve that tracks the position of the probe. This observed dip is due to a reduction or "band-flattening" of the surface electric field due to the presence of carriers generated by the probe. [R. Kudrawiec, et al., "Three beam photo-reflectance as a powerful method to investigate semiconductor heterostructures," *Thin Solid Films* 450, 71-74 (2004) ("Kudrawiec 2004")].

Figure 6:
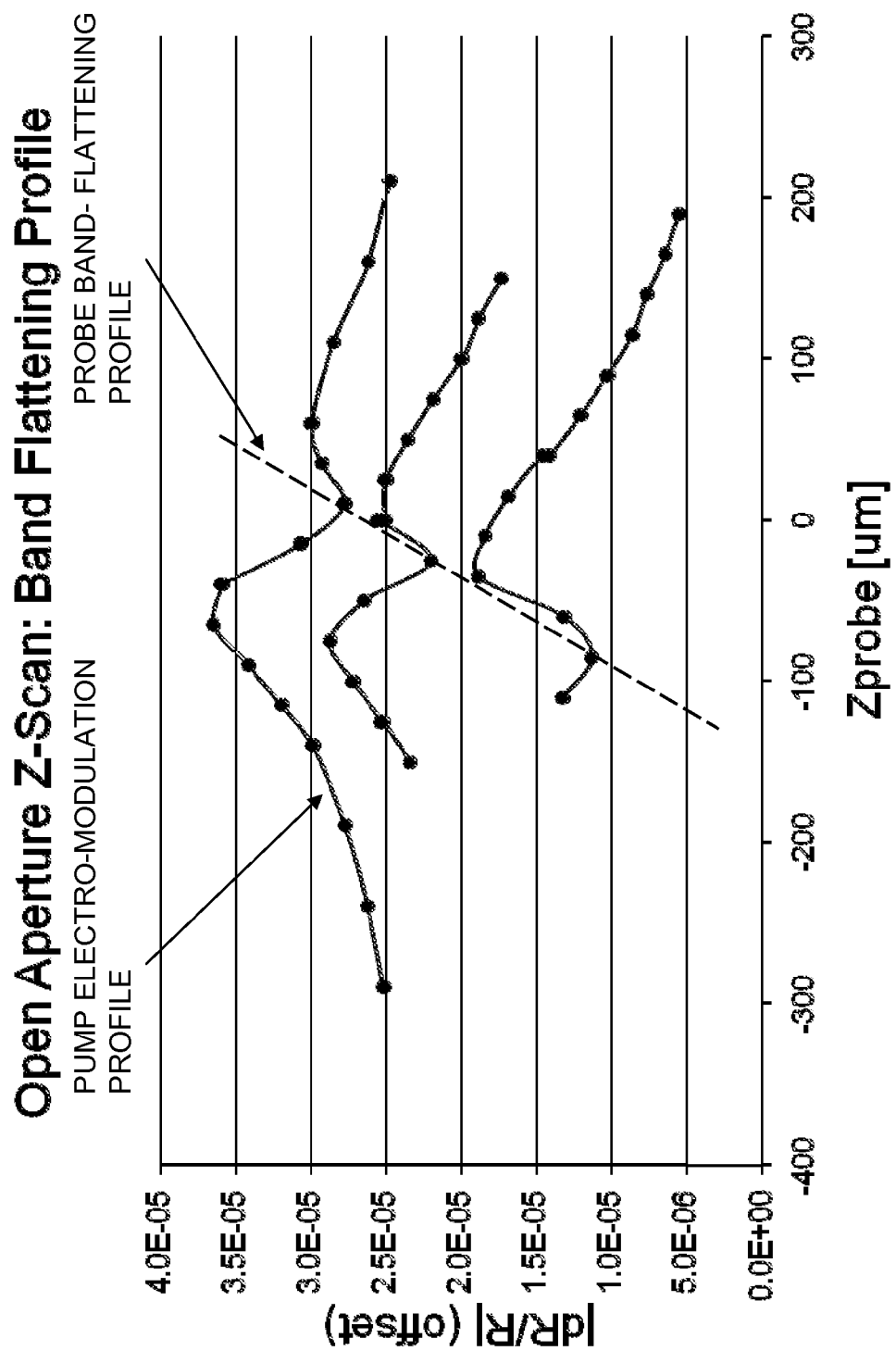
FIG. 6 shows the data of FIG. 3-5 plotted as a function of sample "z," i.e., the distance from the probe waist to the sample surface, for three values of pump-probe offset. The pump induced electro-refraction profile translates with respect to the probe waist.

FIG. 6 shows the data of FIG. 3-5 plotted as a function of sample "z," i.e., the distance from the probe waist to the sample surface, for three values of pump-probe offset. The pump induced electro-refraction profile translates with respect to the probe waist.

Figure 7:
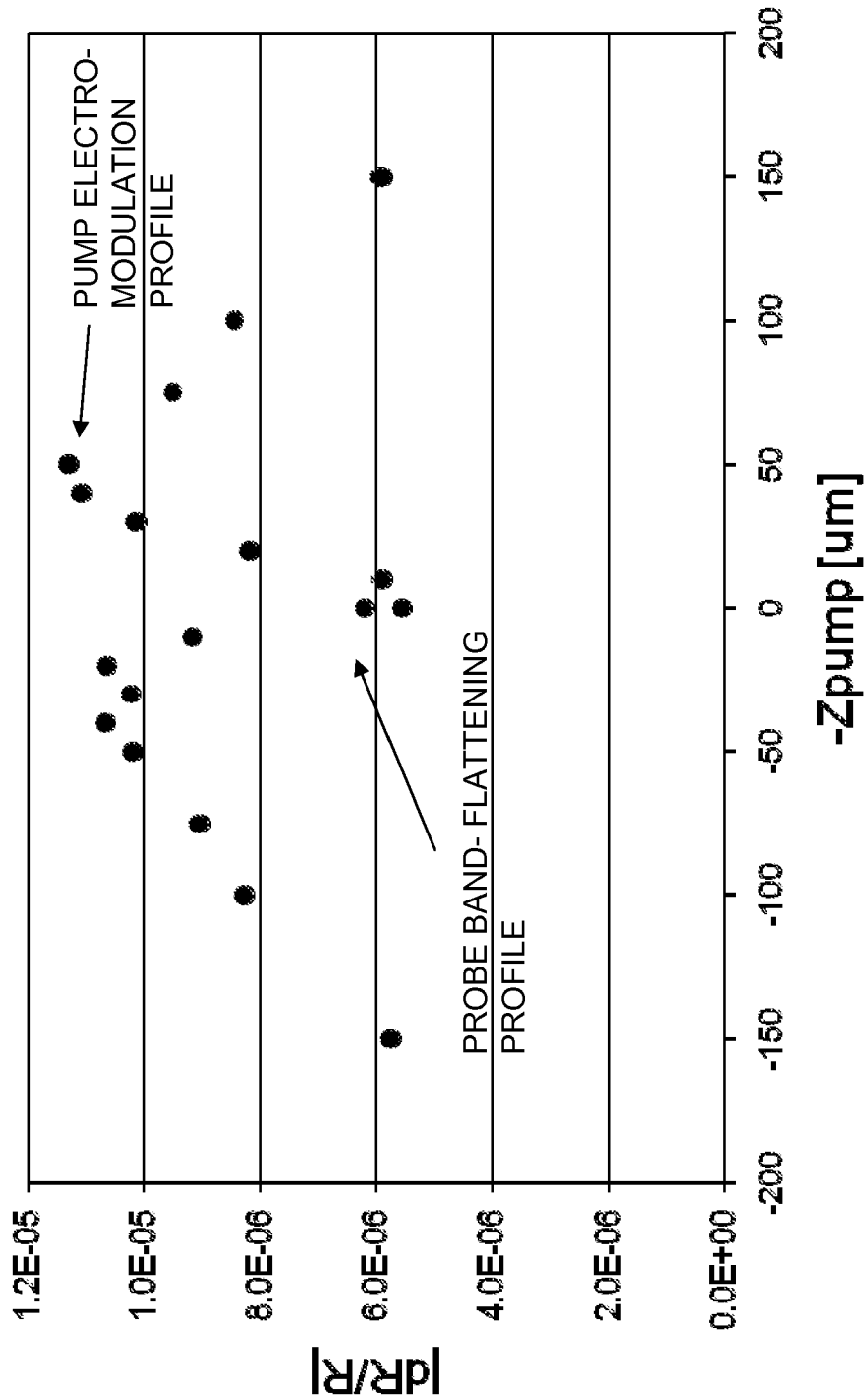
FIG. 7 shows an open aperture z-scan photo-reflectance curve taken on the $n^-/n$ junction sample using a 40× "neofluar" microscope objective. The beam waists are approximately overlapped in the transverse and longitudinal directions. The open aperture z-scan curve exhibits a sharp well-localized dip in z superimposed on a larger more slowly varying photo-reflectance signal. The pump induced electro-refraction profile translates with respect to the probe band-flattening profile.

In certain cases, this probe band flattening profile can be used to directly quantify the active carrier concentration in semiconductor structures. For example, FIG. 7 includes an open aperture z-scan photo-reflectance curve taken on the n⁻/n junction sample using a 40× "neofluar" microscope objective, which provides high transmission at 375 nm. The beam waists are approximately overlapped in the transverse and longitudinal directions, maximizing the probe induced band flattening. The pump and probe focal positions were controlled with independent telescoping lens arrangements in either input beam path, which may be automated.

Photo-reflectance measurements were again performed at a multiplicity of pump waist positions with respect to the sample surface. The open aperture z-scan curve exhibits a dip, localized in z, superimposed on a larger more slowly varying photo-reflectance signal. The position of this dip may be varied by altering the relative position of the probe waist with respect to the pump waist. The phase angle of the photo-reflectance response changed only slightly through each of these scans. The amplitude of the "dip" was proportional to the probe induced reduction in surface charge density, which is of order $1\times10^{19}$ charge carriers per cubic centimeter. This probe band-flattening effect is the same effect as reported using a third CW pump (unmodulated) laser beam to suppress the photo-reflectance signal. [Kudrawiec 2004]. In an embodiment of the instant invention, it is the CW probe beam that results in the "bandflattening" profile $|g(\rho,z)|^2$. This profile is superimposed (as a function of pump-probe focal offset $\Delta z$, and transverse offset $\Delta\rho$) onto the pump induced electro-modulation profile $|f(\rho+\Delta\rho,z+\Delta z)|^2$. The resultant dip provides a natural scale with which to quantify the active dose, since the relative amplitude of the dip with respect to the maximum electro-modulation signal z profile is inversely proportional to surface carrier concentration. For example, the relative size of the dip shown in FIG. 7 indicates the surface carrier concentration of the n⁻/n sample is approximately 2 times the probe induced surface carrier concentration. This provides a means to measure surface carrier concentration without the need for calibration to reference samples.

Figure 8:
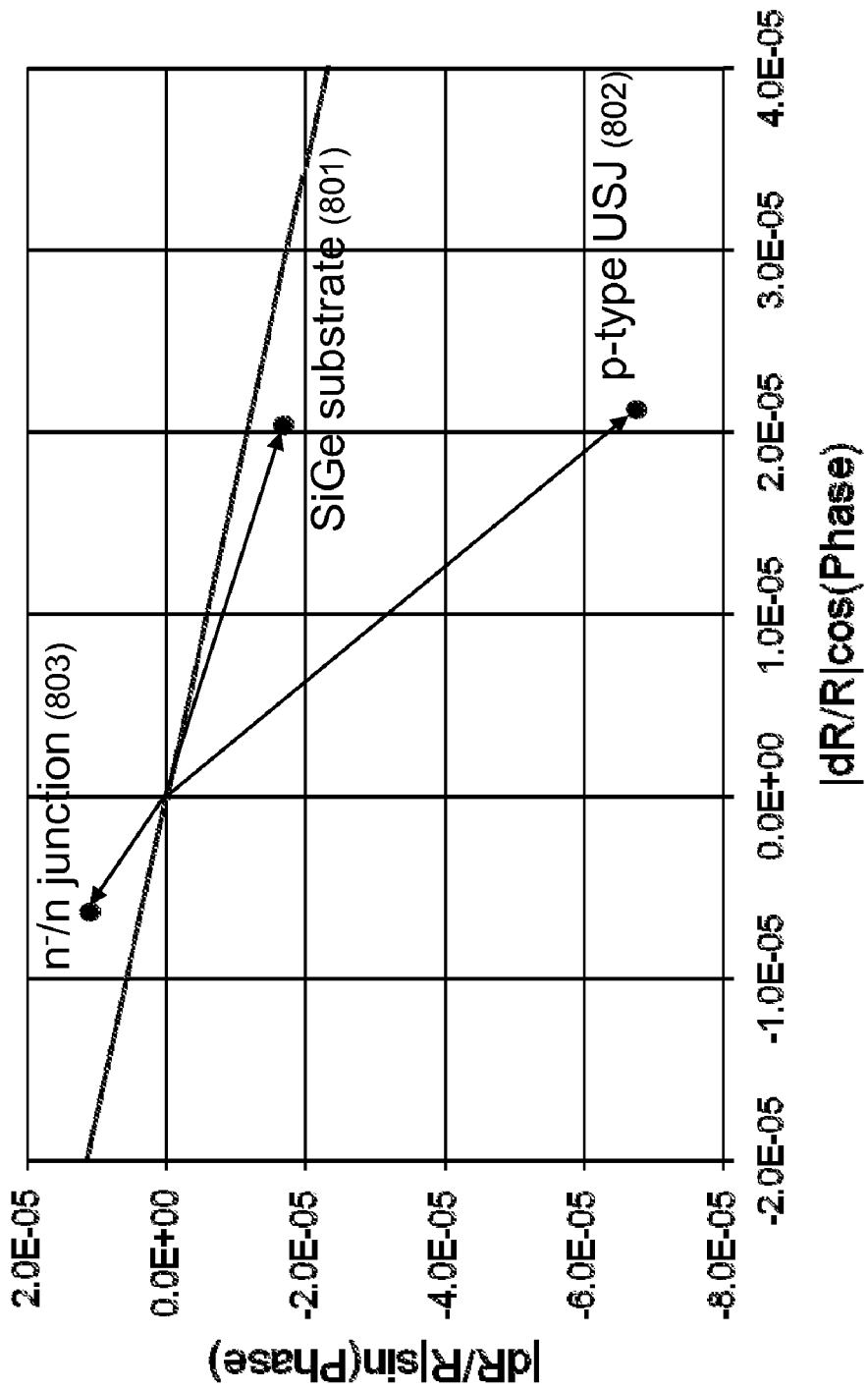
FIG. 8 shows experimental photo-reflectance vector taken with a 20× achromatic objective lens for three silicon semiconductor structures: (i) SiGe substrate; (ii) p-type USJ; and (iii) $n^-/n$ junction. The probe power and focal spot size were configured to minimize the probe band flattening while maintaining sufficient probe light throughput. The amplitude of the PR response is largest on the p-type USJ silicon film structure, due to its large near surface electric field. The photo-reflectance signal from the $n^-/n$ junction shows a phase lag of approximately 30° with respect to the phase of the pump laser modulation. The signal of the p-type USJ structure shows a phase lag of approximately 220°, and the SiGe substrate a phase lag of approximately 190°.

The photo-reflectance amplitude and phase are very sensitive to near surface electric fields in semiconductor structures. FIG. 8 shows experimental photo-reflectance signal taken with a 20× achromatic objective lens for three silicon semiconductor structures: (i) SiGe substrate 801; (ii) p-type USJ 802; and (iii) n⁻/n junction 803. The probe power and focal spot size were configured to minimize the probe band flattening while maintaining sufficient probe light throughput. As shown in FIG. 8, the amplitude of the PR response is largest on the p-type USJ silicon filmstructure, due to its large near surface electric field. The phase of the photo-reflectance response is used to determine the direction of the reflectivity change in response to the pump modulation. The photo-reflectance signal from the n⁻/n junction shows a phase lag of approximately 30° with respect to the phase of the pump laser modulation. The signal of the p-type USJ structure shows a phase lag of approximately 220°, and the SiGe substrate a phase lag of approximately 190°.

The physical interpretation of the photo-reflectance phase reveals the following:

The 30° phase lag of the n⁻/n junction structure corresponds to an increasing reflectivity with the 30° lag being due interaction dynamics, i.e., carrier transport and recombination under the pump-on/pump-off conditions. [H. Shen, et al., "Dynamics of photoreflectance from undoped GaAs," *Appl. Phys. Lett.* 59, 321-323 (1991)].

The 220° lag of the p-type USJ structure is approximately 180° out of phase with the n⁻/n junction and therefore demonstrates a decreasing reflectivity with pump phase. A lag of approximately 40° due the interaction dynamics remains present. The p-type USJ has a much larger electric field than the n⁻/n junction and its near surface electric field is in the opposite direction. Accordingly, when the pump induced modulated band flattening occurs, the near surface electric field is modulated in the opposite direction with respect to the n⁻/n junction, i.e., the field modulation has a different sign, which manifests in the photoreflectance signal as a change vector direction.

For the SiGe substrate, the phase lag is approximately 190°. The interpretation is that the reflectivity again decreases with pump excitation, which produces the 180° shift, and the interaction lag is just ~10°.

Figure 9:
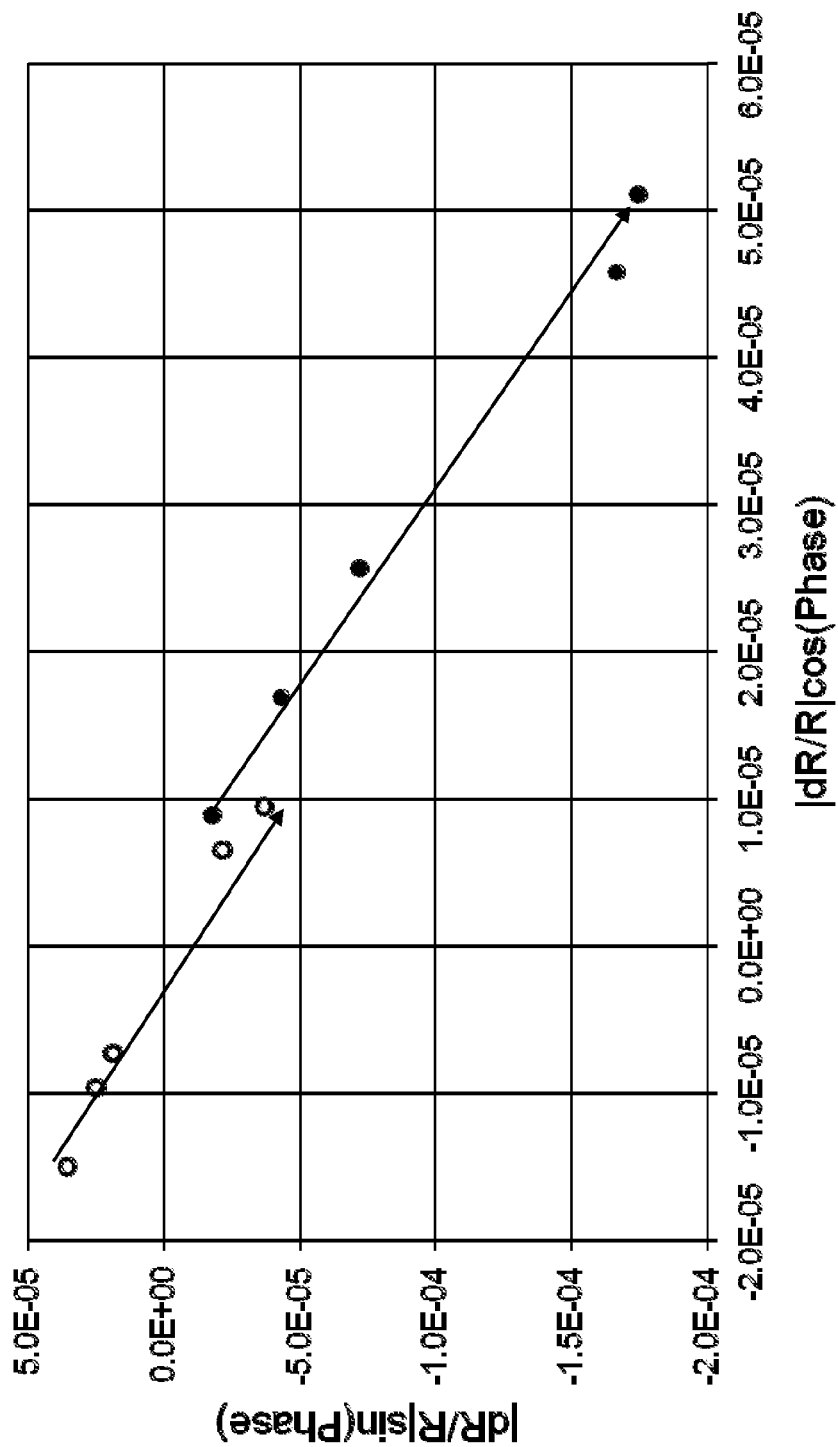
FIG. 9 is a photo-reflectance vector plot of p-type USJ structures flash annealed at a sequence of temperatures. The photo-reflectance vector translates along a line as the flash temp is changed.

FIG. 9 is a vector plot of various p-type USJ structures "flash annealed" at a sequence of temperatures. The samples were processed with millisecond timescale flash anneal processes in the temperature range 1250° C. to 1350° C. The photo-reflectance vector translates along a line as the flash temp is changed. This deterministic behavior is observed on numerous shallow-junction type sample sets. This is further consistent with the interpretation of the PR signal as linearly proportional with near surface carrier concentration as suggested by the Poisson relation [Aspnes 1980].

Figure 10:
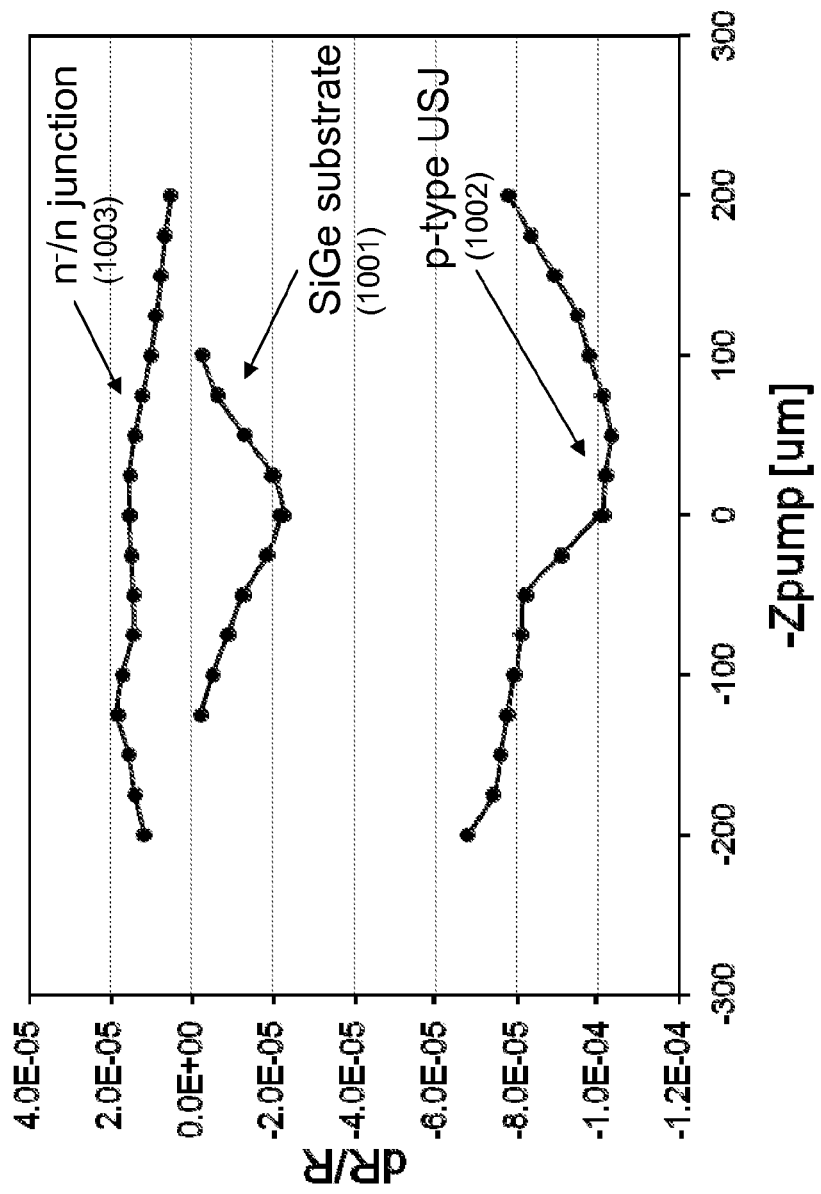
FIG. 10 shows open aperture z-scan photo-reflectance curves taken with a 20× achromatic objective lens for three silicon semiconductor structures: (i) SiGe substrate; (ii) p-type USJ; and (iii) $n^-/n$ junction. The probe power and focal spot size were configured to minimize the probe band flattening while maintaining sufficient probe light throughput. The phase of the photo-reflectance response has been used to determine the direction of the reflectivity change in response to the pump modulation. The z-scan photo-reflectance curves from the $n^-/n$ junction and the p-type USJ structure show relatively broad pump electro-modulation profiles, whereas the SiGe substrate z-scan data exhibits a narrower electro-modulation profile.

FIG. 10 shows open aperture z-scan photo-reflectance curves taken with a 20× achromatic objective lens for three silicon semiconductor structures: (i) SiGe substrate 1001; (ii) p-type USJ 1002; and (iii) n⁻/n junction 1003. The probe power and focal spot size were configured to minimize the probe band flattening while maintaining sufficient probe light throughput. The phase of the photo-reflectance response has been used to determine the direction of the reflectivity change in response to the pump modulation. The z-scan photo-reflectance curves from the n⁻/n junction and the p-type USJ structure show relatively broad pump electro-modulation profiles, whereas the SiGe substrate z-scan data exhibits a narrower electromodulation profile. This is consistent with small phase lag exhibited in the vector plot (FIG. 8), and shows a significantly smaller z-scan interaction range for the SiGe substrate and very little probe band flattening, i.e., the interaction dynamics in the SiGe semiconductor structure happen more quickly and occur over a shorter range than in the p-type USJ or n⁻/n junction structures. From the equation, $n_2 \approx \Delta R/R_{max} \times (n^2-k^2-1)/I_{pump}$, the effective nonlinear refraction $n_2$ for each sample may be estimated. For the p-type USJ, $n_2 \approx -5\times10^{-9}$ cm²/W, whereas for the n⁻/n junction and the SiGe substrate, $n_2 \approx +7.4\times10^{-10}$ cm²/W and $n_2 \approx -1\times10^{-9}$ cm²/W, respectively.

Figure 11:
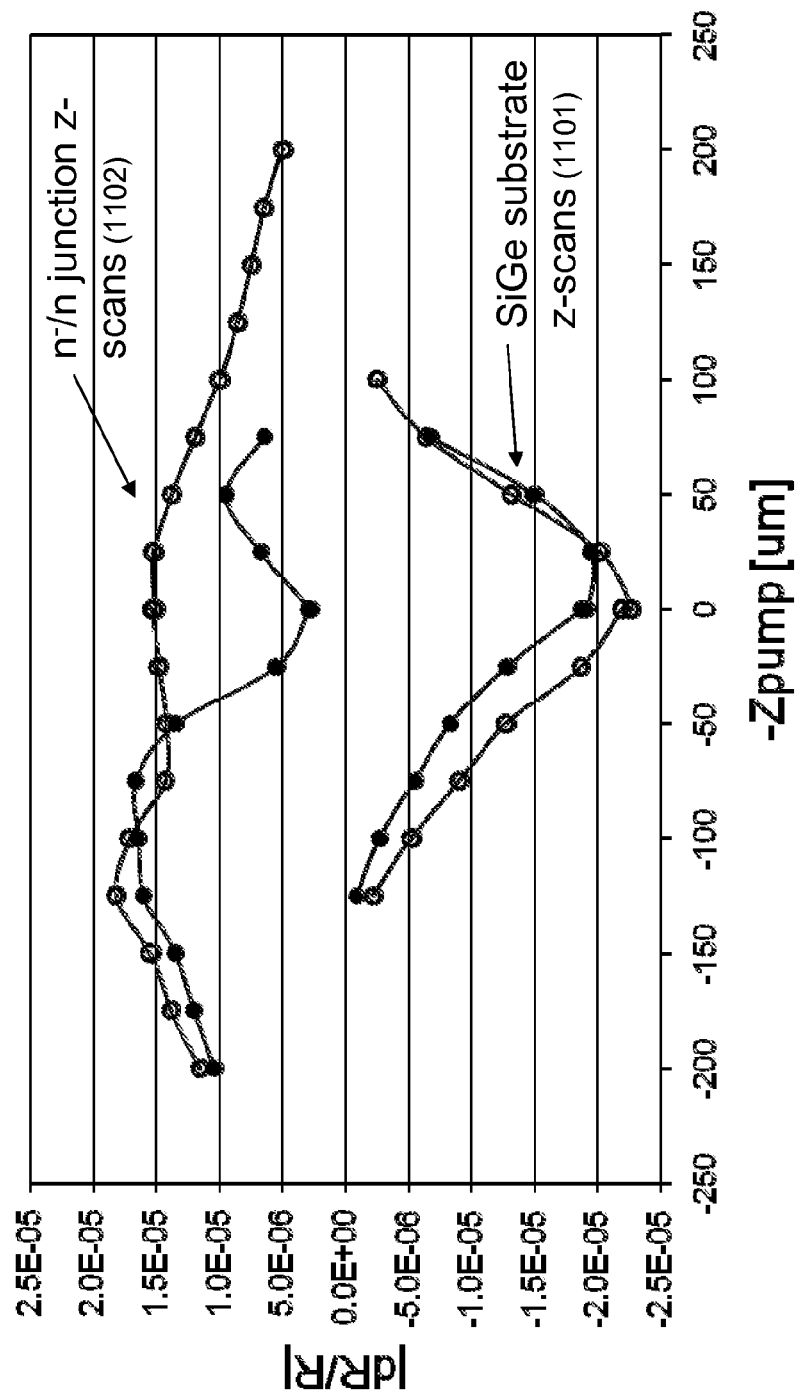
FIG. 11 shows open aperture and small aperture z-scan photo-reflectance curves taken with a 20× achromatic objective lens for the SiGe substrate for the $n^-/n$ junction. Either set of curves exhibits a shift in the small aperture curve near Z=0, implying an "on-axis" shift of the photo-reflectance beam phase front.

In conjunction with the "open-aperture" z-scan, the "on-axis" or small aperture z-scan capability is utilized to characterize the electro-absorptive signature. FIG. 11 shows open aperture and small aperture z-scan photo-reflectance curves taken with a 20× achromatic objective lens for the SiGe substrate 1101 and for the nm junction 1102. The z-scan photo-reflectance data on either sample exhibits a shift and in the small aperture z-scan curve near z=0, implying an "on-axis" shift of the photo-reflectance beam phase front.

Figure 12:
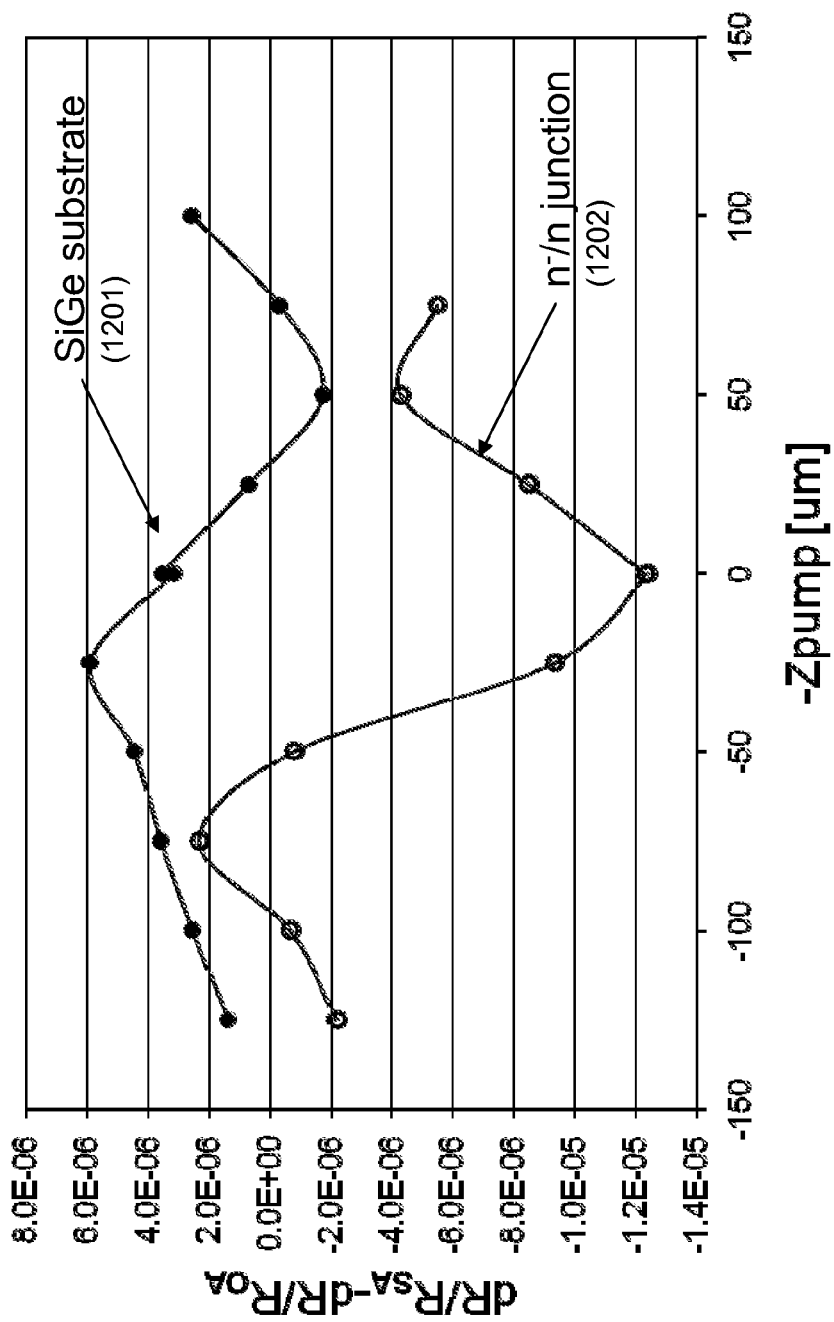
FIG. 12 illustrates the difference of the open aperture and on-axis z-scan for the SiGe substrate and the $n-/n$ junction. From the direction of the "peak-valley" structure of the differenced z-scans, the electroabsorptive nonlinearity for either sample is observed to be of the same sign despite the fact their respective electro-refractive nonlinearities are opposite. The shape corresponds to an increasing electroabsorption or $\Delta k>0$.

FIG. 12 illustrates the difference of the open aperture and on-axis z-scan for the SiGe substrate 1201 and the n⁻/n junction 1202. From the shape of the peak-valley form of the differenced z-scan curves, the electroabsorptive nonlinearity for either sample is observed to be of the same sign, despite the fact their respective electro-refractive nonlinearities are of opposite sign. The shape corresponds to an increasing electroabsorption or $\Delta k>0$. The size of the electro-absorptive effect measured must be calibrated for aperture size. [Ma 1995]. The data above used approximately 50% aperture transmittance. Measurement of the on-axis transmittance is limited in practice by the need for throughput in the photo-reflectance system.

Figure 13:
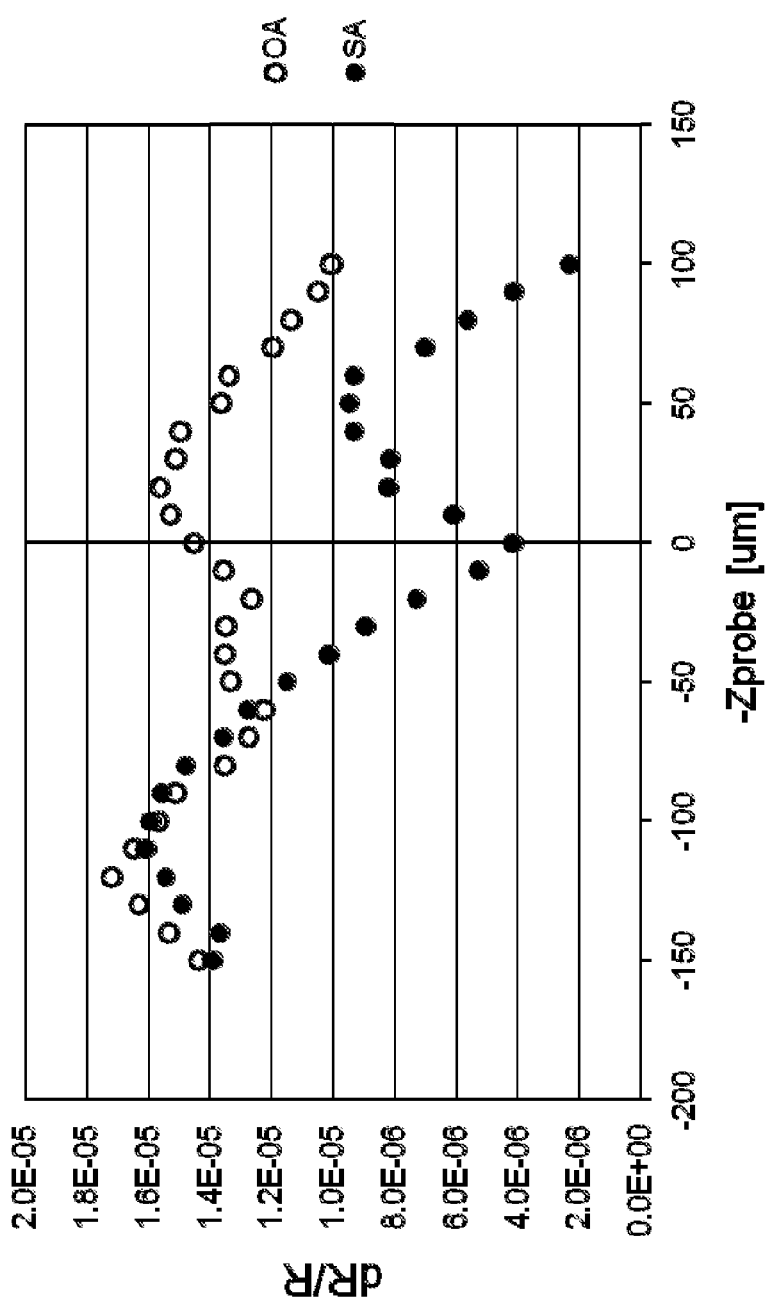
FIG. 13 shows open aperture and "on-axis" z-scans for the e USJ and the $n^-/n$ junction, taken using automated z-stepping and photo-reflectance data acquisition. The $n^-/n$ junction "on axis" curve shows a shift and dip near z=0, indicating a shift of the probe beam phase front.

However, it remains possible to measure small signatures of on-axis phase change even with approximately 50% transmittance. FIG. 13 shows open aperture and "on-axis" z-scans for the $n^-/n$ junction, taken using automated z-stepping and photoreflectance data acquisition. The $n^-/n$ junction "on-axis" curve shows a shift and dip near z=0, again indicating a shift of the photoreflectance beam phase front.

Figure 14:
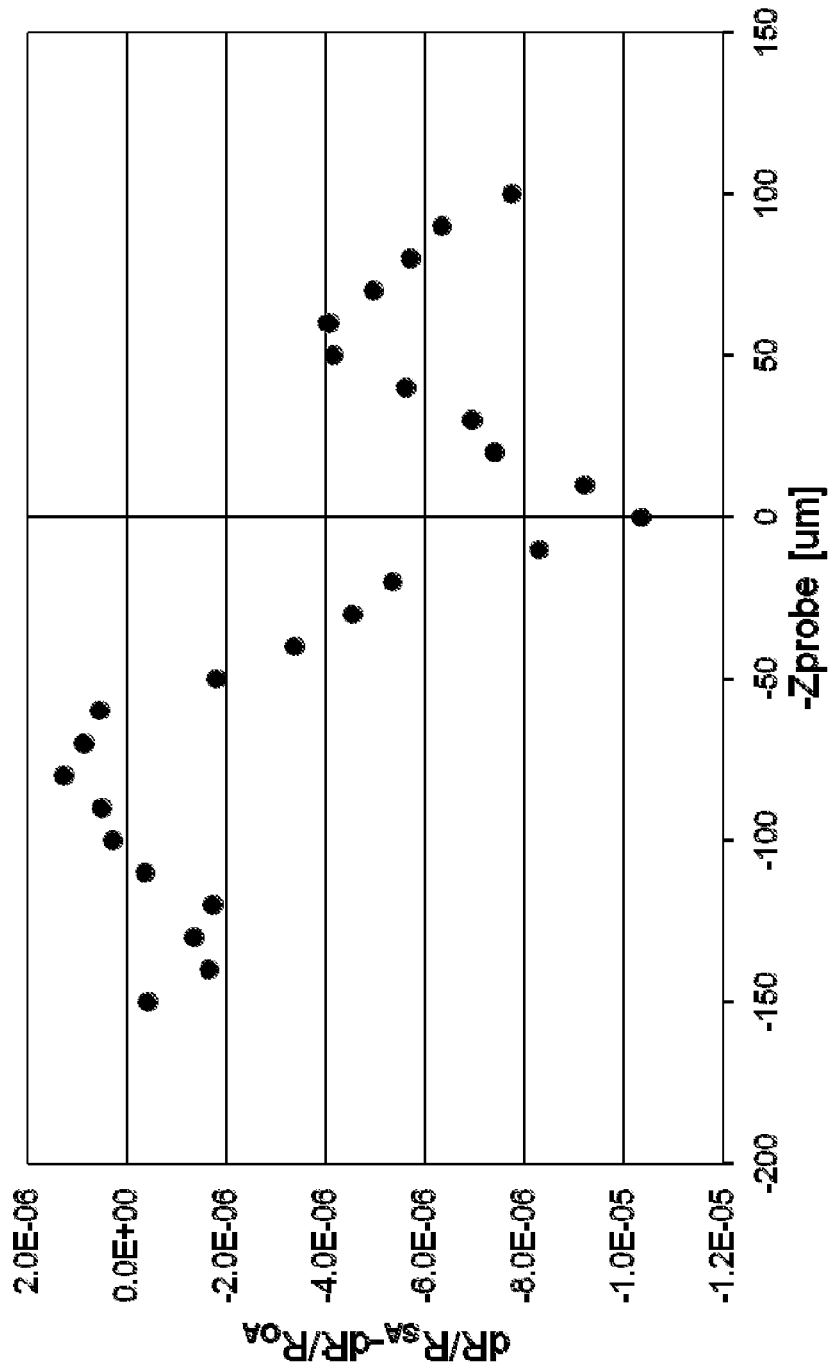
FIG. 14 illustrates the difference of the open aperture and on-axis z-scan curves of FIG. 13. The difference in photo-reflectance amplitude across the "peak-valley" signature, $\Delta T_{p-v}$, matches with $\Delta T_{p-v}$ reported for the $n-/n$ junction structure in FIG. 12.

FIG. 14 illustrates the difference of the open aperture and on-axis z-scan curves of FIG. 13. Here, the size of the effective nonlinear extinction coefficient is determined by the amplitude of the peak-valley z-scan signature and the sign of the effective nonlinear extinction is determined by the direction of the peak-valley signature. As noted, the observed shape corresponds to $\Delta k>0$. The magnitude of the effective nonlinear extinction may be estimated from the equation $k_2 \approx \Delta T_{p-v} \times 10^{-1} \times (n^2-k^21)/I_{pump} 6 \times 10^{12}$ cm$^2$/W where $\Delta T_{p-v} \sim 1.2 \times 10^{-6}$, as shown in FIG. 14, and the factor of $10^{-1}$ roughly accounts for the 50% aperture condition. More precise quantification of the electro-absorptive nonlinearity may be achieved using a fit to Equation (8). [Petrov 1994]. The sign and magnitude of the measured nonlinear refractions and absorptions on the samples reported herein is consistent with expectations from consideration of the location of the probe laser wavelength in respect to the Si $E_1$ absorption. For example, the derivative of $\in_2$ at the probe wavelength is small (approaching zero), whereas the derivative of $\in_1$ is maximal, implying $\Delta \in_1 >> \Delta \in_2$ (as observed). Thus, by performing open aperture and on-axis z-scan photo-reflectance measurements, independent measurement of the electro-refractive and electroabsorptive components of photo-reflectance is attained.

As to a further discussion of the manner of usage and operation of the present invention, the same should be apparent from the above description.

With respect to the above description then, it is to be realized that the optimum dimensional relationships for the parts of the invention, to include variations in size, materials, shape, form, function and manner of operation, assembly and use, are deemed readily apparent to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Accordingly, the scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

What is claimed is:

1. A method of z-scan photo-reflectance characterization of a semiconductor structure, the method comprising the steps of:
   (a) illuminating an area of a surface of the semiconductor structure using an amplitude modulated pump laser beam, wherein
      (i) the pump laser beam comprises at least one wavelength with energy greater than the smallest interband transition energy of a semiconductor material within the semiconductor structure, thereby inducing time periodic changes in electronic charge density within the semiconductor structure such that the electric field profile within the semiconductor structure obtains a time periodic modulation, and
      (ii) the semiconductor material within the semiconductor structure is subject to a time periodic modulation of interband transition energies;
   (b) illuminating a portion of said modulated electric field profile of step (a) with a separate probe laser beam, wherein the probe laser beam comprises at least one wavelength
      (i) nearby an interband transition energy of the semiconductor material within the semiconductor structure, and
      (ii) suitable for recording the induced changes in semiconductor material optical response which occur nearby to interband transition energies;
   (c) recording reflected alternating current probe light from the illumination of the semiconductor structure, wherein the alternating current probe light comprises a photo-reflectance signal;
   (d) performing a series of photo-reflectance measurements of steps (a), (b), and (c), with the semiconductor structure at a multiplicity of positions along the focal length of the probe light column, wherein an aperture is fixtured in the far field of the probe laser beam;
   (e) using the information collected in steps (a), (b), (c), and (d) to determine a physical property of the semiconductor structure, including at least one of a nonlinear refraction or a nonlinear absorption.

2. The method of claim 1, wherein the semiconductor structure comprises a material selected from the group consisting of II-VI zincblende semiconductor material, silicon, silicon-germanium, III-V semiconductor material, gallium arsenide, gallium nitride, carbon, germanium, silicon carbide, boron, nitrogen, phosphorus, arsenic, and combinations thereof.

3. The method of claim 1, wherein the semiconductor structure comprises a semiconductor electronic interface selected from the group consisting of a p-n junction, a p$^+$/p junction, a n-p junction, a n$^-$/n junction, p-type ultra shallow junction, n-type ultra shallow junction, and combinations thereof.

4. The method of claim 1, wherein the semiconductor structure comprises a field selected from the group consisting of a surface band bending electric field, a near surface electric field arising from an electronic interface, and combinations thereof.

5. The method of claim 1 further comprising determining changes in the photo-reflectance signal as a function of intensity or profile of the pump laser beam.

6. The method of claim 1 further comprising determining changes in the photo-reflectance signal as a function of the intensity or profile of the probe laser beam.

7. The method of claim 1, wherein the wavelength of the probe laser is in the range selected from the group consisting of (a) 360 nm to 380 nm and (b) 395 nm to 415 nm.

8. The method of claim 1, wherein the aperture in the far field of the reflected probe beam is fixtured to provide on-axis light transmission in the range of 10 percent to 100 percent.

9. The method of claim 1 further comprising
(i) acquiring the photo-reflectance signal using an open aperture z-scan, and
(ii) determining pump induced nonlinear refraction from the photo-reflectance signal.

10. The method of claim 9, wherein the surface carrier concentration is determined from the probe band flattening profile.

11. The method of claim 1 further comprising
(i) acquiring the photo-reflectance signal using an restricted aperture z-scan, and
(ii) determining pump induced nonlinear absorption from the photo-reflectance signal.

12. The method of claim 1, wherein pump induced nonlinear absorption is determined from the difference of open aperture and restricted aperture z-scan photo-reflectance curves.

13. The method of claim 1 further comprising determining nonlinear refraction according to an empirically determined calibration curve.

14. The method of claim 1 further comprising determining nonlinear absorption according to an empirically determined calibration curve.

15. The method of claim 1 further comprising determining electric field depth profile according to an empirically determined calibration curve.

16. The method of claim 1 further comprising using z-scan photo-reflectance information to determine pump induced electric field profile as a function of an offset selected from the group consisting of pump-probe focus offsets, transverse offsets, and combinations thereof.

17. An apparatus for detecting physical properties of a semiconductor structure, comprising:
(a) a pump laser system, wherein the pump laser system is operable
(i) to provide an amplitude modulated laser beam with a modulation frequency in the range of 100 kHz to 50 MHz,
(ii) to operate at optical powers of at least about approximately 5 mW, and
(iii) to contain at least one wavelength with energy greater than the smallest interband transition energy of a semiconductor material within the semiconductor structure;
(b) a probe laser system, wherein the probe laser system is operable
(i) to provide a continuous wave laser beam,
(ii) to operate at optical powers of at most about approximately 15 mW, and
(iii) to contain at least one wavelength nearby an interband transition energy of a semiconductor material within the semiconductor structure;
(c) a photoreceiver operable to generate an electrical current proportional to input intensity;
(d) an optical system, wherein the optical system is operable
(i) to focus at least one of the amplitude modulated laser beam and the continuous wave laser beam onto a common focal position on a surface of the semiconductor structure of diameter at most 50 microns,
(ii) to translate the common focal position through a distance of approximately 10 times the Rayleigh range of at least one of the amplitude modulated laser beam and the continuous wave laser beam, and
(iii) to separate and direct probe light reflected from the semiconductor structure through an aperture fixtured in a far field of the continuous wave laser beam and into the photoreceiver;
(e) a phase locked signal detection system operable to record output of the photoreceiver; and
(f) a computer comprising measurement and system control software.

18. The apparatus of claim 17, wherein the optical system comprises a telescoping lens arrangement operable to control pump-probe focal offset, wherein the telescoping lens arrangement is fixtured in the input path of the amplitude modulated laser beam or the continuous wave laser beam.

19. The apparatus of claim 17, wherein the optical system comprises a beam expander fixture in the reflected probe light path operable to expand and collimate the probe beam before transmission through the aperture.

20. The apparatus of claim 17, wherein the probe laser wavelength is approximately 375 nm.

* * * * *